United States Patent
Wei

(10) Patent No.: US 8,560,082 B2
(45) Date of Patent: Oct. 15, 2013

(54) COMPUTERIZED DETERMINATION OF INSULIN PUMP THERAPY PARAMETERS USING REAL TIME AND RETROSPECTIVE DATA PROCESSING

(75) Inventor: Charles Wei, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1079 days.

(21) Appl. No.: 12/363,714

(22) Filed: Jan. 30, 2009

(65) Prior Publication Data

US 2010/0198314 A1 Aug. 5, 2010

(51) Int. Cl.
*A61N 1/00* (2006.01)

(52) U.S. Cl.
USPC .......................................................... 607/67

(58) Field of Classification Search
USPC .......................................................... 607/67
See application file for complete search history.

(56) References Cited

U.S. PATENT DOCUMENTS

| | | | |
|---|---|---|---|
| 2,915,579 A | 12/1959 | Mendelsohn | |
| 3,374,337 A | 3/1968 | Burley | |
| 3,510,747 A | 5/1970 | Petrides | |
| 3,606,592 A | 9/1971 | Madurski et al. | |
| 3,750,687 A | 8/1973 | Williams | |
| 3,843,455 A | 10/1974 | Bier | |
| 3,923,060 A | 12/1975 | Elinwood | |
| 3,930,493 A | 1/1976 | Williamson | |
| 3,994,799 A | 11/1976 | Yao et al. | |
| 4,018,547 A | 4/1977 | Rogen | |
| 4,048,551 A | 9/1977 | Bosik | |
| 4,121,282 A | 10/1978 | Ohsawa | |
| 4,146,029 A | 3/1979 | Elinwood | |
| 4,193,397 A | 3/1980 | Tucker et al. | |
| 4,268,173 A | 5/1981 | Barnard et al. | |
| 4,288,793 A | 9/1981 | Lotscher | |
| 4,362,052 A | 12/1982 | Heath et al. | |
| 4,401,122 A | 8/1983 | Clark, Jr. | |
| 4,439,197 A | 3/1984 | Honda et al. | |
| 4,447,224 A | 5/1984 | DeCant, Jr. et al. | |

(Continued)

FOREIGN PATENT DOCUMENTS

| | | |
|---|---|---|
| AU | 2003/259741 | 2/2004 |
| CA | 2495648 | 2/2004 |

(Continued)

OTHER PUBLICATIONS

"An Electrochemical Slow Flow Meter", http://gore.ocean.washington.edu/research/slow_flow_meter.html, 2005, 3 pages.

(Continued)

*Primary Examiner* — Joseph Dietrich
(74) *Attorney, Agent, or Firm* — Jackson & Co., LLP

(57) ABSTRACT

Methods and devices for providing computerized adjustment to therapy parameters using real time and retrospective data processing is provided. Embodiments include receiving a respective data set from an infusion device and an analyte monitoring device for a predetermined time duration, user notification and reminder of the predetermined time duration, time synchronizing the received respective data set, detecting one or more marked data from the one or more respective data set received, establishing one or more filtering criteria to filter of retrospective or historical data based on certain condition, performing automated data analysis based on the detected one or more marked data or the data achieving certain predetermined condition to generate a modification to a therapy profile, generating and modifying rules for profile modification, and providing the generated modification to the therapy profile for reporting and transmission.

29 Claims, 14 Drawing Sheets

(56) References Cited

U.S. PATENT DOCUMENTS

| | | |
|---|---|---|
| 4,458,686 A | 7/1984 | Clark, Jr. |
| 4,467,811 A | 8/1984 | Clark, Jr. |
| 4,472,113 A | 9/1984 | Rogen |
| 4,494,950 A | 1/1985 | Fischell |
| 4,512,348 A | 4/1985 | Uchigaki et al. |
| 4,524,343 A | 6/1985 | Morgan et al. |
| 4,529,401 A | 7/1985 | Leslie et al. |
| 4,531,235 A | 7/1985 | Brusen |
| 4,562,751 A | 1/1986 | Nason et al. |
| 4,563,249 A | 1/1986 | Hale |
| 4,570,492 A | 2/1986 | Walsh |
| 4,573,994 A | 3/1986 | Fischell et al. |
| 4,633,878 A | 1/1987 | Bombardieri |
| 4,678,408 A | 7/1987 | Nason et al. |
| 4,685,903 A | 8/1987 | Cable et al. |
| 4,686,624 A | 8/1987 | Blum et al. |
| 4,736,748 A | 4/1988 | Nakamura et al. |
| 4,755,173 A | 7/1988 | Konopka et al. |
| 4,811,564 A | 3/1989 | Palmer |
| 4,850,959 A | 7/1989 | Findl |
| 4,851,827 A | 7/1989 | Nicholas |
| 4,866,396 A | 9/1989 | Tamura |
| 4,890,621 A | 1/1990 | Hakky |
| 4,953,552 A | 9/1990 | DeMarzo |
| 4,976,590 A | 12/1990 | Baldwin |
| 4,979,509 A | 12/1990 | Hakky |
| 4,984,581 A | 1/1991 | Stice |
| 5,004,532 A | 4/1991 | Hale et al. |
| 5,012,667 A | 5/1991 | Kruse |
| 5,019,974 A | 5/1991 | Beckers |
| 5,036,861 A | 8/1991 | Sembrowich et al. |
| 5,051,880 A | 9/1991 | Harm et al. |
| 5,061,914 A | 10/1991 | Bush et al. |
| 5,079,920 A | 1/1992 | Whitehead et al. |
| 5,081,421 A | 1/1992 | Miller et al. |
| 5,101,814 A | 4/1992 | Palti |
| 5,124,661 A | 6/1992 | Zelin et al. |
| 5,139,023 A | 8/1992 | Stanley et al. |
| 5,155,695 A | 10/1992 | Stein |
| 5,190,041 A | 3/1993 | Palti |
| 5,205,819 A | 4/1993 | Ross et al. |
| 5,207,666 A | 5/1993 | Idriss et al. |
| 5,211,371 A | 5/1993 | Coffee |
| 5,211,626 A | 5/1993 | Frank et al. |
| 5,223,822 A | 6/1993 | Stommes et al. |
| 5,262,305 A | 11/1993 | Heller et al. |
| 5,267,026 A | 11/1993 | Kawahara et al. |
| 5,278,997 A | 1/1994 | Martin |
| 5,284,423 A | 2/1994 | Holdsworth et al. |
| 5,291,614 A | 3/1994 | Baker et al. |
| 5,291,887 A | 3/1994 | Stanley et al. |
| 5,324,599 A | 6/1994 | Oyama et al. |
| 5,325,280 A | 6/1994 | Tortola et al. |
| 5,349,852 A | 9/1994 | Kamen et al. |
| 5,356,786 A | 10/1994 | Heller et al. |
| 5,366,292 A | 11/1994 | Voss |
| 5,368,028 A | 11/1994 | Palti |
| 5,371,687 A | 12/1994 | Holmes, II et al. |
| 5,372,133 A | 12/1994 | Hogen Esch |
| 5,376,070 A | 12/1994 | Purvis et al. |
| 5,382,331 A | 1/1995 | Banks |
| 5,390,671 A | 2/1995 | Lord et al. |
| 5,391,250 A | 2/1995 | Cheney, II et al. |
| 5,398,681 A | 3/1995 | Kuperschmidt |
| 5,404,585 A | 4/1995 | Vimpari et al. |
| 5,406,301 A | 4/1995 | Ravid |
| 5,445,611 A | 8/1995 | Eppstein et al. |
| 5,448,992 A | 9/1995 | Kuperschmidt |
| 5,458,140 A | 10/1995 | Eppstein et al. |
| 5,469,025 A | 11/1995 | Kanemori et al. |
| 5,479,486 A | 12/1995 | Saji |
| 5,494,562 A | 2/1996 | Maley et al. |
| 5,497,772 A | 3/1996 | Schulman et al. |
| 5,505,713 A | 4/1996 | Van Antwerp |
| 5,507,288 A | 4/1996 | Bocker et al. |
| 5,517,434 A | 5/1996 | Hanson et al. |
| 5,526,844 A | 6/1996 | Kamen et al. |
| 5,533,389 A | 7/1996 | Kamen et al. |
| 5,543,678 A | 8/1996 | Hoiberg |
| 5,559,528 A | 9/1996 | Ravid |
| 5,568,400 A | 10/1996 | Stark et al. |
| 5,568,806 A | 10/1996 | Cheney, II et al. |
| 5,575,770 A | 11/1996 | Melsky et al. |
| 5,576,535 A | 11/1996 | Oosterwijk et al. |
| 5,586,553 A | 12/1996 | Halili et al. |
| 5,593,852 A | 1/1997 | Heller et al. |
| 5,594,906 A | 1/1997 | Holmes, II et al. |
| 5,601,435 A | 2/1997 | Quy |
| 5,604,404 A | 2/1997 | Sahara |
| 5,615,671 A | 4/1997 | Schoonen et al. |
| 5,622,413 A | 4/1997 | Kim et al. |
| 5,622,482 A | 4/1997 | Lee |
| 5,640,954 A | 6/1997 | Pfeiffer et al. |
| 5,645,709 A | 7/1997 | Birch et al. |
| 5,660,163 A | 8/1997 | Schulman et al. |
| 5,661,643 A | 8/1997 | Blakely et al. |
| 5,662,461 A | 9/1997 | Ono |
| 5,671,301 A | 9/1997 | Kuperschmidt |
| 5,685,844 A | 11/1997 | Marttila |
| 5,695,949 A | 12/1997 | Galen et al. |
| 5,703,928 A | 12/1997 | Galloway et al. |
| 5,707,502 A | 1/1998 | McCaffrey et al. |
| 5,708,247 A | 1/1998 | McAleer et al. |
| 5,711,861 A | 1/1998 | Ward et al. |
| 5,711,868 A | 1/1998 | Maley et al. |
| 5,722,397 A | 3/1998 | Eppstein |
| 5,741,211 A | 4/1998 | Renirie et al. |
| 5,748,872 A | 5/1998 | Norman |
| 5,759,510 A | 6/1998 | Pillai |
| 5,771,890 A | 6/1998 | Tamada |
| 5,774,254 A | 6/1998 | Berlin |
| 5,786,439 A | 7/1998 | Van Antwerp et al. |
| 5,790,297 A | 8/1998 | Berlin |
| 5,791,344 A | 8/1998 | Schulman et al. |
| 5,814,599 A | 9/1998 | Mitragotri et al. |
| 5,815,303 A | 9/1998 | Berlin |
| 5,822,715 A | 10/1998 | Worthington et al. |
| 5,825,488 A | 10/1998 | Kohl et al. |
| 5,848,990 A | 12/1998 | Cirelli et al. |
| 5,851,197 A | 12/1998 | Marano et al. |
| 5,873,026 A | 2/1999 | Reames |
| 5,875,417 A | 2/1999 | Golden |
| 5,885,211 A | 3/1999 | Eppstein et al. |
| 5,899,855 A | 5/1999 | Brown |
| 5,913,833 A | 6/1999 | Elstrom et al. |
| 5,918,603 A | 7/1999 | Brown |
| 5,923,512 A | 7/1999 | Brownlow et al. |
| 5,947,921 A | 9/1999 | Johnson et al. |
| 5,948,512 A | 9/1999 | Kubota et al. |
| 5,951,582 A | 9/1999 | Thorne et al. |
| 5,951,836 A | 9/1999 | McAleer et al. |
| 5,954,643 A | 9/1999 | Van Antwerp et al. |
| 5,965,380 A | 10/1999 | Heller et al. |
| 5,968,011 A | 10/1999 | Larsen et al. |
| 5,971,922 A | 10/1999 | Arita et al. |
| 6,001,067 A | 12/1999 | Shults et al. |
| 6,002,961 A | 12/1999 | Mitragotri et al. |
| 6,011,486 A | 1/2000 | Casey |
| 6,014,577 A | 1/2000 | Henning et al. |
| 6,017,328 A | 1/2000 | Fischell et al. |
| 6,018,678 A | 1/2000 | Mitragotri et al. |
| 6,023,629 A | 2/2000 | Tamada |
| 6,024,539 A | 2/2000 | Blomquist et al. |
| 6,026,320 A | 2/2000 | Carlson et al. |
| 6,027,459 A | 2/2000 | Shain et al. |
| 6,027,496 A | 2/2000 | Loomis et al. |
| 6,027,692 A | 2/2000 | Galen et al. |
| 6,032,059 A | 2/2000 | Henning et al. |
| 6,041,253 A | 3/2000 | Kost et al. |
| 6,041,665 A | 3/2000 | Hussain |
| 6,059,546 A | 5/2000 | Brenan et al. |
| 6,063,039 A | 5/2000 | Cunningham et al. |
| 6,064,368 A | 5/2000 | Kang |
| 6,066,243 A | 5/2000 | Anderson et al. |

(56) References Cited

U.S. PATENT DOCUMENTS

| | | | |
|---|---|---|---|
| 6,067,017 | A | 5/2000 | Stewart et al. |
| 6,067,463 | A | 5/2000 | Jeng et al. |
| 6,071,249 | A | 6/2000 | Cunningham et al. |
| 6,071,251 | A | 6/2000 | Cunningham et al. |
| 6,073,031 | A | 6/2000 | Helstab et al. |
| 6,077,660 | A | 6/2000 | Wong et al. |
| 6,081,104 | A | 6/2000 | Kern |
| 6,083,710 | A | 7/2000 | Heller et al. |
| 6,085,871 | A | 7/2000 | Karamata |
| 6,086,575 | A | 7/2000 | Mejslov |
| 6,091,975 | A | 7/2000 | Daddona et al. |
| 6,093,156 | A | 7/2000 | Cunningham et al. |
| 6,093,172 | A | 7/2000 | Funderburk et al. |
| 6,121,009 | A | 9/2000 | Heller et al. |
| 6,129,823 | A | 10/2000 | Hughes et al. |
| 6,132,371 | A | 10/2000 | Dempsey et al. |
| 6,142,939 | A | 11/2000 | Eppstein et al. |
| 6,144,303 | A | 11/2000 | Federman |
| 6,144,869 | A | 11/2000 | Berner et al. |
| 6,144,922 | A | 11/2000 | Douglas et al. |
| 6,147,342 | A | 11/2000 | Kucher |
| 6,154,855 | A | 11/2000 | Norman |
| 6,155,992 | A | 12/2000 | Henning et al. |
| 6,157,442 | A | 12/2000 | Raskas |
| 6,160,449 | A | 12/2000 | Klomsdorf et al. |
| 6,162,202 | A | 12/2000 | Sicurelli et al. |
| 6,162,611 | A | 12/2000 | Heller et al. |
| 6,164,284 | A | 12/2000 | Schulman et al. |
| 6,173,160 | B1 | 1/2001 | Liimatainen |
| 6,175,752 | B1 | 1/2001 | Say et al. |
| 6,180,416 | B1 | 1/2001 | Kurnik et al. |
| 6,185,452 | B1 | 2/2001 | Schulman et al. |
| 6,201,980 | B1 | 3/2001 | Darrow et al. |
| 6,206,841 | B1 | 3/2001 | Cunningham et al. |
| 6,208,894 | B1 | 3/2001 | Schulman et al. |
| 6,212,416 | B1 | 4/2001 | Ward et al. |
| 6,215,206 | B1 | 4/2001 | Chitayat |
| 6,222,514 | B1 | 4/2001 | DeLuca |
| 6,228,100 | B1 | 5/2001 | Schraga |
| 6,232,370 | B1 | 5/2001 | Kubota et al. |
| 6,233,471 | B1 | 5/2001 | Berner et al. |
| 6,233,539 | B1 | 5/2001 | Brown |
| 6,242,961 | B1 | 6/2001 | Liu et al. |
| 6,245,060 | B1 | 6/2001 | Loomis et al. |
| 6,248,067 | B1 | 6/2001 | Causey, III et al. |
| 6,262,708 | B1 | 7/2001 | Chu |
| 6,272,364 | B1 | 8/2001 | Kurnik |
| 6,278,425 | B1 | 8/2001 | DeLuca |
| 6,280,587 | B1 | 8/2001 | Matsumoto |
| 6,283,926 | B1 | 9/2001 | Cunningham et al. |
| 6,284,478 | B1 | 9/2001 | Heller et al. |
| 6,288,653 | B1 | 9/2001 | Shih |
| 6,293,925 | B1 | 9/2001 | Safabash et al. |
| 6,295,506 | B1 | 9/2001 | Heinonen et al. |
| 6,298,254 | B2 | 10/2001 | Tamada |
| 6,298,255 | B1 | 10/2001 | Cordero et al. |
| 6,299,578 | B1 | 10/2001 | Kurnik et al. |
| 6,301,499 | B1 | 10/2001 | Carlson et al. |
| 6,306,104 | B1 | 10/2001 | Cunningham et al. |
| 6,309,351 | B1 | 10/2001 | Kurnik et al. |
| 6,312,888 | B1 | 11/2001 | Wong et al. |
| 6,315,721 | B2 | 11/2001 | Schulman et al. |
| 6,326,160 | B1 | 12/2001 | Dunn et al. |
| 6,329,161 | B1 | 12/2001 | Heller et al. |
| 6,341,232 | B1 | 1/2002 | Conn et al. |
| 6,356,776 | B1 | 3/2002 | Berner et al. |
| 6,360,888 | B1 | 3/2002 | McIvor et al. |
| 6,366,793 | B1 | 4/2002 | Bell et al. |
| 6,368,141 | B1 | 4/2002 | Van Antwerp et al. |
| 6,368,274 | B1 | 4/2002 | Van Antwerp et al. |
| 6,372,371 | B1 | 4/2002 | Iarochenko et al. |
| 6,375,344 | B1 | 4/2002 | Hanson et al. |
| 6,375,638 | B2 | 4/2002 | Nason et al. |
| 6,377,894 | B1 | 4/2002 | Deweese et al. |
| 6,379,301 | B1 | 4/2002 | Worthington et al. |
| 6,381,496 | B1 | 4/2002 | Meadows et al. |
| 6,393,318 | B1 | 5/2002 | Conn et al. |
| 6,403,944 | B1 | 6/2002 | MacKenzie et al. |
| 6,405,066 | B1 | 6/2002 | Essenpreis et al. |
| 6,408,402 | B1 | 6/2002 | Norman |
| 6,417,074 | B2 | 7/2002 | Kopley et al. |
| 6,419,642 | B1 | 7/2002 | Marchitto et al. |
| 6,425,829 | B1 | 7/2002 | Julien |
| 6,427,088 | B1 | 7/2002 | Bowman, IV et al. |
| 6,432,585 | B1 | 8/2002 | Kawakami et al. |
| 6,437,379 | B2 | 8/2002 | Kopley et al. |
| 6,438,385 | B1 | 8/2002 | Heinonen et al. |
| 6,438,414 | B1 | 8/2002 | Conn et al. |
| 6,442,413 | B1 | 8/2002 | Silver |
| 6,461,329 | B1 | 10/2002 | Van Antwerp et al. |
| 6,462,162 | B2 | 10/2002 | Van Antwerp et al. |
| 6,464,848 | B1 | 10/2002 | Matsumoto |
| 6,466,807 | B1 | 10/2002 | Dobson et al. |
| 6,466,810 | B1 | 10/2002 | Ward et al. |
| 6,468,222 | B1 | 10/2002 | Mault et al. |
| 6,471,980 | B2 | 10/2002 | Sirhan et al. |
| 6,472,991 | B1 | 10/2002 | Schulman et al. |
| 6,475,196 | B1 | 11/2002 | Vachon |
| 6,478,736 | B1 | 11/2002 | Mault |
| 6,480,730 | B2 | 11/2002 | Darrow et al. |
| 6,482,158 | B2 | 11/2002 | Mault |
| 6,484,045 | B1 | 11/2002 | Holker et al. |
| 6,485,138 | B1 | 11/2002 | Kubota et al. |
| 6,485,461 | B1 | 11/2002 | Mason et al. |
| 6,492,180 | B2 | 12/2002 | Brown et al. |
| 6,506,168 | B1 | 1/2003 | Fathallah et al. |
| 6,513,532 | B2 | 2/2003 | Mault et al. |
| 6,514,460 | B1 | 2/2003 | Fendrock |
| 6,514,689 | B2 | 2/2003 | Han et al. |
| 6,514,718 | B2 | 2/2003 | Heller et al. |
| 6,522,530 | B2 | 2/2003 | Bang |
| 6,525,330 | B2 | 2/2003 | Paolini et al. |
| 6,526,298 | B1 | 2/2003 | Khalil et al. |
| 6,529,772 | B2 | 3/2003 | Carlson et al. |
| 6,530,915 | B1 | 3/2003 | Eppstein et al. |
| 6,535,753 | B1 | 3/2003 | Raskas |
| 6,537,243 | B1 | 3/2003 | Henning et al. |
| 6,540,675 | B2 | 4/2003 | Aceti et al. |
| 6,540,891 | B1 | 4/2003 | Stewart et al. |
| 6,543,224 | B1 | 4/2003 | Barooah |
| 6,544,212 | B2 | 4/2003 | Galley et al. |
| 6,546,269 | B1 | 4/2003 | Kurnik |
| 6,549,796 | B2 | 4/2003 | Sohrab |
| 6,551,276 | B1 | 4/2003 | Mann et al. |
| 6,554,798 | B1 | 4/2003 | Mann et al. |
| 6,558,320 | B1 | 5/2003 | Causey, III et al. |
| 6,558,321 | B1 | 5/2003 | Burd et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,564,105 | B2 | 5/2003 | Starkweather et al. |
| 6,564,807 | B1 | 5/2003 | Schulman et al. |
| 6,565,509 | B1 | 5/2003 | Say et al. |
| 6,565,738 | B1 | 5/2003 | Henning et al. |
| 6,569,157 | B1 | 5/2003 | Shain et al. |
| 6,571,128 | B2 | 5/2003 | Lebel et al. |
| 6,571,200 | B1 | 5/2003 | Mault |
| 6,576,117 | B1 | 6/2003 | Iketaki et al. |
| 6,577,899 | B2 | 6/2003 | Lebel et al. |
| 6,579,498 | B1 | 6/2003 | Eglise |
| 6,579,690 | B1 | 6/2003 | Bonnacaze et al. |
| 6,582,393 | B2 | 6/2003 | Sage, Jr. |
| 6,585,644 | B2 | 7/2003 | Lebel et al. |
| 6,586,971 | B1 | 7/2003 | Naffziger et al. |
| 6,587,705 | B1 | 7/2003 | Kim et al. |
| 6,589,229 | B1 | 7/2003 | Connelly et al. |
| 6,594,514 | B2 | 7/2003 | Berner et al. |
| 6,595,919 | B2 | 7/2003 | Berner et al. |
| 6,596,016 | B1 | 7/2003 | Vreman et al. |
| 6,600,997 | B2 | 7/2003 | Deweese et al. |
| 6,602,469 | B1 | 8/2003 | Maus et al. |
| 6,607,509 | B2 | 8/2003 | Bobroff et al. |
| 6,610,012 | B2 | 8/2003 | Mault |

(56) References Cited

U.S. PATENT DOCUMENTS

| | | |
|---|---|---|
| 6,612,306 B1 | 9/2003 | Mault |
| 6,615,061 B1 | 9/2003 | Khalil et al. |
| 6,615,074 B2 | 9/2003 | Mickle et al. |
| 6,618,603 B2 | 9/2003 | Varalli et al. |
| 6,620,106 B2 | 9/2003 | Mault |
| 6,623,501 B2 | 9/2003 | Heller et al. |
| 6,629,934 B2 | 10/2003 | Mault et al. |
| 6,633,095 B1 | 10/2003 | Swope et al. |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,645,142 B2 | 11/2003 | Braig et al. |
| 6,648,821 B2 | 11/2003 | Lebel et al. |
| 6,650,064 B2 | 11/2003 | Guthrie et al. |
| 6,653,091 B1 | 11/2003 | Dunn et al. |
| 6,656,114 B1 | 12/2003 | Poulson et al. |
| 6,656,158 B2 | 12/2003 | Mahoney et al. |
| 6,656,159 B2 | 12/2003 | Flaherty |
| 6,658,396 B1 | 12/2003 | Tang et al. |
| 6,659,948 B2 | 12/2003 | Lebel et al. |
| 6,668,196 B1 | 12/2003 | Villegas et al. |
| 6,669,663 B1 | 12/2003 | Thompson |
| 6,669,669 B2 | 12/2003 | Flaherty et al. |
| 6,670,806 B2 | 12/2003 | Wendt et al. |
| 6,675,030 B2 | 1/2004 | Ciuczak et al. |
| 6,679,841 B2 | 1/2004 | Bojan et al. |
| 6,687,522 B2 | 2/2004 | Tamada |
| 6,687,546 B2 | 2/2004 | Lebel et al. |
| 6,692,457 B2 | 2/2004 | Flaherty |
| 6,694,191 B2 | 2/2004 | Starkweather et al. |
| 6,695,885 B2 | 2/2004 | Schulman et al. |
| 6,699,218 B2 | 3/2004 | Flaherty et al. |
| 6,702,857 B2 | 3/2004 | Brauker et al. |
| 6,723,072 B2 | 4/2004 | Flaherty et al. |
| 6,728,560 B2 | 4/2004 | Kollias et al. |
| 6,730,200 B1 | 5/2004 | Stewart et al. |
| 6,731,976 B2 | 5/2004 | Penn et al. |
| 6,733,446 B2 | 5/2004 | Lebel et al. |
| 6,736,777 B2 | 5/2004 | Kim et al. |
| 6,736,797 B1 | 5/2004 | Larsen et al. |
| 6,738,654 B2 | 5/2004 | Sohrab |
| 6,740,059 B2 | 5/2004 | Flaherty |
| 6,740,075 B2 | 5/2004 | Lebel et al. |
| 6,741,877 B1 | 5/2004 | Shults et al. |
| 6,743,635 B2 | 6/2004 | Neel et al. |
| 6,749,587 B2 | 6/2004 | Flaherty |
| 6,752,787 B1 | 6/2004 | Causey, III et al. |
| 6,758,810 B2 | 7/2004 | Lebel et al. |
| 6,764,581 B1 | 7/2004 | Forrow et al. |
| 6,768,425 B2 | 7/2004 | Flaherty et al. |
| 6,770,030 B1 | 8/2004 | Schaupp et al. |
| 6,770,729 B2 | 8/2004 | Van Antwerp |
| 6,773,563 B2 | 8/2004 | Matsumoto |
| 6,779,984 B2 | 8/2004 | Lilie et al. |
| 6,790,178 B1 | 9/2004 | Mault et al. |
| 6,794,195 B2 | 9/2004 | Colvin, Jr. |
| 6,799,861 B2 | 10/2004 | Naghi et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,816,742 B2 | 11/2004 | Kim et al. |
| 6,818,348 B1 | 11/2004 | Venkatesan et al. |
| 6,830,558 B2 | 12/2004 | Flaherty et al. |
| 6,832,114 B1 | 12/2004 | Whitehurst et al. |
| 6,833,540 B2 | 12/2004 | MacKenzie et al. |
| 6,835,553 B2 | 12/2004 | Han et al. |
| 6,837,858 B2 | 1/2005 | Cunningham et al. |
| 6,839,596 B2 | 1/2005 | Nelson et al. |
| 6,840,912 B2 | 1/2005 | Kloepfer et al. |
| 6,849,237 B2 | 2/2005 | Housefield et al. |
| 6,850,790 B2 | 2/2005 | Berner et al. |
| 6,859,831 B1 | 2/2005 | Gelvin et al. |
| 6,862,465 B2 | 3/2005 | Shults et al. |
| 6,872,200 B2 | 3/2005 | Mann et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,893,396 B2 | 5/2005 | Schulze et al. |
| 6,895,265 B2 | 5/2005 | Silver |
| 6,898,451 B2 | 5/2005 | Wuori |
| 6,899,683 B2 | 5/2005 | Mault et al. |
| 6,899,684 B2 | 5/2005 | Mault et al. |
| 6,904,301 B2 | 6/2005 | Raskas |
| 6,907,127 B1 | 6/2005 | Kravitz et al. |
| 6,908,535 B2 | 6/2005 | Rankin et al. |
| 6,916,159 B2 | 7/2005 | Rush et al. |
| 6,918,874 B1 | 7/2005 | Hatch et al. |
| 6,922,576 B2 | 7/2005 | Raskas |
| 6,922,578 B2 | 7/2005 | Eppstein et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,936,029 B2 | 8/2005 | Mann et al. |
| 6,949,816 B2 | 9/2005 | Brown et al. |
| 6,950,708 B2 | 9/2005 | Bowman, IV et al. |
| 6,952,603 B2 | 10/2005 | Gerber et al. |
| 6,955,650 B2 | 10/2005 | Mault et al. |
| 6,958,129 B2 | 10/2005 | Galen et al. |
| 6,958,705 B2 | 10/2005 | Lebel et al. |
| 6,960,192 B1 | 11/2005 | Flaherty et al. |
| 6,974,437 B2 | 12/2005 | Lebel et al. |
| 6,979,326 B2 | 12/2005 | Mann et al. |
| 6,990,366 B2 | 1/2006 | Say et al. |
| 6,990,372 B2 | 1/2006 | Perron et al. |
| 6,997,911 B2 | 2/2006 | Klitmose |
| 6,997,920 B2 | 2/2006 | Mann et al. |
| 6,999,810 B2 | 2/2006 | Berner et al. |
| 7,003,340 B2 | 2/2006 | Say et al. |
| 7,003,341 B2 | 2/2006 | Say et al. |
| 7,005,857 B2 | 2/2006 | Stiene et al. |
| 7,006,858 B2 | 2/2006 | Silver et al. |
| 7,010,356 B2 | 3/2006 | Jog et al. |
| 7,011,630 B2 | 3/2006 | Desai et al. |
| 7,018,360 B2 | 3/2006 | Flaherty et al. |
| 7,020,508 B2 | 3/2006 | Stirovic et al. |
| 7,024,245 B2 | 4/2006 | Lebel et al. |
| 7,024,249 B2 | 4/2006 | Weisner et al. |
| 7,025,743 B2 | 4/2006 | Mann et al. |
| 7,029,444 B2 | 4/2006 | Shin et al. |
| 7,029,455 B2 | 4/2006 | Flaherty |
| 7,034,677 B2 | 4/2006 | Steinthal et al. |
| 7,041,468 B2 | 5/2006 | Drucker et al. |
| 7,043,287 B1 | 5/2006 | Khalil et al. |
| 7,052,251 B2 | 5/2006 | Nason et al. |
| 7,067,498 B2 | 6/2006 | Wolf et al. |
| 7,070,591 B2 | 7/2006 | Adams et al. |
| 7,072,738 B2 | 7/2006 | Bonney et al. |
| 7,074,307 B2 | 7/2006 | Simpson et al. |
| 7,077,328 B2 | 7/2006 | Krishnaswamy et al. |
| 7,079,901 B1 | 7/2006 | Loftin et al. |
| 7,081,195 B2 | 7/2006 | Simpson et al. |
| 7,083,593 B2 | 8/2006 | Stultz |
| 7,086,277 B2 | 8/2006 | Tess et al. |
| 7,092,762 B1 | 8/2006 | Loftin et al. |
| 7,092,891 B2 | 8/2006 | Maus et al. |
| 7,097,983 B2 | 8/2006 | Markovsky et al. |
| 7,098,803 B2 | 8/2006 | Mann et al. |
| 7,108,711 B2 | 9/2006 | Vogel et al. |
| 7,108,778 B2 | 9/2006 | Simpson et al. |
| 7,110,803 B2 | 9/2006 | Shults et al. |
| 7,114,502 B2 | 10/2006 | Schulman et al. |
| 7,123,206 B2 | 10/2006 | Hess et al. |
| 7,133,710 B2 | 11/2006 | Acosta et al. |
| 7,134,999 B2 | 11/2006 | Brauker et al. |
| 7,136,689 B2 | 11/2006 | Shults et al. |
| 7,136,704 B2 | 11/2006 | Schulman |
| 7,137,964 B2 | 11/2006 | Flaherty |
| 7,144,384 B2 | 12/2006 | Gorman et al. |
| 7,149,581 B2 | 12/2006 | Goedeke |
| 7,153,212 B1 | 12/2006 | Karten et al. |
| 7,154,398 B2 | 12/2006 | Chen et al. |
| 7,163,511 B2 | 1/2007 | Conn et al. |

(56) References Cited

U.S. PATENT DOCUMENTS

| | | |
|---|---|---|
| 7,167,818 B2 | 1/2007 | Brown |
| 7,171,274 B2 | 1/2007 | Starkweather et al. |
| 7,181,261 B2 | 2/2007 | Silver et al. |
| 7,186,566 B2 | 3/2007 | Qian |
| 7,186,791 B2 | 3/2007 | Bruno et al. |
| 7,192,450 B2 | 3/2007 | Brauker et al. |
| 7,198,603 B2 | 4/2007 | Penner et al. |
| 7,202,734 B1 | 4/2007 | Raab |
| 7,205,409 B2 | 4/2007 | Pei et al. |
| 7,208,119 B1 | 4/2007 | Kurtock et al. |
| 7,211,048 B1 | 5/2007 | Najafi et al. |
| 7,218,017 B1 | 5/2007 | Chitayet et al. |
| 7,225,535 B2 | 6/2007 | Feldman et al. |
| 7,226,278 B2 | 6/2007 | Nason et al. |
| 7,226,442 B2 | 6/2007 | Sheppard, Jr. et al. |
| 7,226,978 B2 | 6/2007 | Tapsak et al. |
| 7,258,666 B2 | 8/2007 | Brown |
| 7,266,400 B2 | 9/2007 | Fine et al. |
| 7,276,029 B2 | 10/2007 | Goode, Jr. et al. |
| 7,283,867 B2 | 10/2007 | Strother et al. |
| 7,299,080 B2 | 11/2007 | Acosta et al. |
| 7,303,549 B2 | 12/2007 | Flaherty et al. |
| 7,310,544 B2 | 12/2007 | Brister et al. |
| 7,323,091 B1 | 1/2008 | Gillette et al. |
| 7,324,949 B2 | 1/2008 | Bristol et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,404,796 B2 | 7/2008 | Ginsberg |
| 7,424,318 B2 | 9/2008 | Brister et al. |
| 7,436,511 B2 | 10/2008 | Ruchti et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,480,138 B2 | 1/2009 | Kogan et al. |
| 7,494,465 B2 | 2/2009 | Brister et al. |
| 7,497,827 B2 | 3/2009 | Brister et al. |
| 7,510,526 B2 | 3/2009 | Merry et al. |
| 7,519,408 B2 | 4/2009 | Rasdal et al. |
| 7,583,190 B2 | 9/2009 | Reggiardo et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,620,437 B2 | 11/2009 | Reggiardo |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0016682 A1 | 8/2001 | Berner et al. |
| 2001/0016683 A1 | 8/2001 | Darrow et al. |
| 2001/0016710 A1 | 8/2001 | Nason et al. |
| 2001/0020124 A1 | 9/2001 | Tamada |
| 2001/0023095 A1 | 9/2001 | Kopley et al. |
| 2001/0024864 A1 | 9/2001 | Kopley et al. |
| 2001/0029340 A1 | 10/2001 | Mault et al. |
| 2001/0034502 A1 | 10/2001 | Moberg et al. |
| 2001/0037060 A1 | 11/2001 | Thompson et al. |
| 2001/0037069 A1 | 11/2001 | Carlson et al. |
| 2001/0041830 A1 | 11/2001 | Varalli et al. |
| 2001/0044581 A1 | 11/2001 | Mault |
| 2001/0044588 A1 | 11/2001 | Mault |
| 2001/0049470 A1 | 12/2001 | Mault et al. |
| 2001/0053891 A1 | 12/2001 | Ackley |
| 2001/0056255 A1 | 12/2001 | Kost et al. |
| 2002/0002326 A1 | 1/2002 | Causey, III et al. |
| 2002/0002328 A1 | 1/2002 | Tamada |
| 2002/0004640 A1 | 1/2002 | Conn et al. |
| 2002/0010414 A1 | 1/2002 | Coston et al. |
| 2002/0019022 A1 | 2/2002 | Dunn et al. |
| 2002/0026937 A1 | 3/2002 | Mault |
| 2002/0027164 A1 | 3/2002 | Mault et al. |
| 2002/0028995 A1 | 3/2002 | Mault |
| 2002/0032374 A1 | 3/2002 | Holker et al. |
| 2002/0040208 A1 | 4/2002 | Flaherty et al. |
| 2002/0042090 A1 | 4/2002 | Heller et al. |
| 2002/0047867 A1 | 4/2002 | Mault et al. |
| 2002/0053637 A1 | 5/2002 | Conn et al. |
| 2002/0062069 A1 | 5/2002 | Mault |
| 2002/0068858 A1 | 6/2002 | Braig et al. |
| 2002/0077765 A1 | 6/2002 | Mault |
| 2002/0077766 A1 | 6/2002 | Mault |
| 2002/0087056 A1 | 7/2002 | Aceti et al. |
| 2002/0091312 A1 | 7/2002 | Berner et al. |
| 2002/0091454 A1 | 7/2002 | Vasko |
| 2002/0103425 A1 | 8/2002 | Mault |
| 2002/0107433 A1 | 8/2002 | Mault |
| 2002/0107476 A1 | 8/2002 | Mann et al. |
| 2002/0109600 A1 | 8/2002 | Mault et al. |
| 2002/0118090 A1 | 8/2002 | Park et al. |
| 2002/0119711 A1 | 8/2002 | Van Antwerp et al. |
| 2002/0124017 A1 | 9/2002 | Mault |
| 2002/0133378 A1 | 9/2002 | Mault et al. |
| 2002/0161286 A1 | 10/2002 | Gerber et al. |
| 2002/0169394 A1 | 11/2002 | Eppstein et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0009133 A1 | 1/2003 | Ramey |
| 2003/0023182 A1 | 1/2003 | Mault et al. |
| 2003/0023317 A1 | 1/2003 | Brauker et al. |
| 2003/0028089 A1 | 2/2003 | Galley et al. |
| 2003/0028120 A1 | 2/2003 | Mault et al. |
| 2003/0032868 A1 | 2/2003 | Graskov et al. |
| 2003/0032874 A1 | 2/2003 | Rhodes et al. |
| 2003/0040683 A1 | 2/2003 | Rule et al. |
| 2003/0050546 A1 | 3/2003 | Desai et al. |
| 2003/0050575 A1 | 3/2003 | Diermann et al. |
| 2003/0060692 A1 | 3/2003 | Ruchti et al. |
| 2003/0060765 A1 | 3/2003 | Campbell et al. |
| 2003/0065257 A1 | 4/2003 | Mault et al. |
| 2003/0065273 A1 | 4/2003 | Mault et al. |
| 2003/0065274 A1 | 4/2003 | Mault et al. |
| 2003/0065275 A1 | 4/2003 | Mault et al. |
| 2003/0065308 A1 | 4/2003 | Lebel et al. |
| 2003/0078560 A1 | 4/2003 | Miller et al. |
| 2003/0100040 A1 | 5/2003 | Bonnacaze et al. |
| 2003/0100821 A1 | 5/2003 | Heller et al. |
| 2003/0105407 A1 | 6/2003 | Pearce, Jr. et al. |
| 2003/0107487 A1 | 6/2003 | Korman et al. |
| 2003/0108976 A1 | 6/2003 | Braig et al. |
| 2003/0118460 A1 | 6/2003 | Lilie et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0135100 A1 | 7/2003 | Kim et al. |
| 2003/0135333 A1 | 7/2003 | Aceti et al. |
| 2003/0153820 A1 | 8/2003 | Berner et al. |
| 2003/0153821 A1 | 8/2003 | Berner et al. |
| 2003/0158472 A1 | 8/2003 | Sohrab |
| 2003/0158707 A1 | 8/2003 | Doi |
| 2003/0175806 A1 | 9/2003 | Rule et al. |
| 2003/0176933 A1 | 9/2003 | Lebel et al. |
| 2003/0181851 A1 | 9/2003 | Mann et al. |
| 2003/0181852 A1 | 9/2003 | Mann et al. |
| 2003/0187338 A1 | 10/2003 | Say et al. |
| 2003/0187525 A1 | 10/2003 | Mann et al. |
| 2003/0191376 A1 | 10/2003 | Samuels et al. |
| 2003/0191431 A1 | 10/2003 | Mann et al. |
| 2003/0195403 A1 | 10/2003 | Berner et al. |
| 2003/0195462 A1 | 10/2003 | Mann et al. |
| 2003/0198558 A1 | 10/2003 | Nason et al. |
| 2003/0199825 A1 | 10/2003 | Flaherty |
| 2003/0199837 A1 | 10/2003 | Vachon |
| 2003/0208110 A1 | 11/2003 | Mault et al. |
| 2003/0208113 A1 | 11/2003 | Mault et al. |
| 2003/0208133 A1 | 11/2003 | Mault |

(56) References Cited

U.S. PATENT DOCUMENTS

| | | |
|---|---|---|
| 2003/0208154 A1 | 11/2003 | Close et al. |
| 2003/0208409 A1 | 11/2003 | Mault |
| 2003/0212346 A1 | 11/2003 | Yuzhakov et al. |
| 2003/0212364 A1 | 11/2003 | Mann et al. |
| 2003/0212379 A1 | 11/2003 | Bylund et al. |
| 2003/0217966 A1 | 11/2003 | Tapsak et al. |
| 2003/0225360 A1 | 12/2003 | Eppstein et al. |
| 2003/0225361 A1 | 12/2003 | Sabra |
| 2003/0226695 A1 | 12/2003 | Mault |
| 2003/0232370 A1 | 12/2003 | Trifiro |
| 2003/0235817 A1 | 12/2003 | Bartkowiak et al. |
| 2004/0010186 A1 | 1/2004 | Kimball et al. |
| 2004/0011671 A1 | 1/2004 | Shults et al. |
| 2004/0018486 A1 | 1/2004 | Dunn et al. |
| 2004/0019321 A1 | 1/2004 | Sage et al. |
| 2004/0027253 A1 | 2/2004 | Marsh et al. |
| 2004/0039256 A1 | 2/2004 | Kawatahara et al. |
| 2004/0045879 A1 | 3/2004 | Shults et al. |
| 2004/0054263 A1 | 3/2004 | Moerman et al. |
| 2004/0059201 A1 | 3/2004 | Ginsberg |
| 2004/0064133 A1 | 4/2004 | Miller et al. |
| 2004/0072357 A1 | 4/2004 | Stiene et al. |
| 2004/0073095 A1 | 4/2004 | Causey, III et al. |
| 2004/0085215 A1 | 5/2004 | Moberg et al. |
| 2004/0096959 A1 | 5/2004 | Stiene et al. |
| 2004/0100376 A1 | 5/2004 | Lye et al. |
| 2004/0106858 A1 | 6/2004 | Say et al. |
| 2004/0106859 A1 | 6/2004 | Say et al. |
| 2004/0106860 A1 | 6/2004 | Say et al. |
| 2004/0108226 A1 | 6/2004 | Polychronakos et al. |
| 2004/0115067 A1 | 6/2004 | Rush et al. |
| 2004/0122353 A1 | 6/2004 | Shahmirian et al. |
| 2004/0132220 A1 | 7/2004 | Fish |
| 2004/0133092 A1 | 7/2004 | Kain |
| 2004/0152622 A1 | 8/2004 | Keith et al. |
| 2004/0158137 A1 | 8/2004 | Eppstein et al. |
| 2004/0162473 A1 | 8/2004 | Sohrab |
| 2004/0164961 A1 | 8/2004 | Bal et al. |
| 2004/0167383 A1 | 8/2004 | Kim et al. |
| 2004/0167801 A1 | 8/2004 | Say et al. |
| 2004/0171921 A1 | 9/2004 | Say et al. |
| 2004/0176913 A1 | 9/2004 | Kawatahara et al. |
| 2004/0186362 A1 | 9/2004 | Brauker et al. |
| 2004/0186365 A1 | 9/2004 | Jin et al. |
| 2004/0193025 A1 | 9/2004 | Steil et al. |
| 2004/0193090 A1 | 9/2004 | Lebel et al. |
| 2004/0199059 A1 | 10/2004 | Brauker et al. |
| 2004/0202576 A1 | 10/2004 | Aceti et al. |
| 2004/0207054 A1 | 10/2004 | Brown et al. |
| 2004/0208780 A1 | 10/2004 | Faries, Jr. et al. |
| 2004/0210184 A1 | 10/2004 | Kost et al. |
| 2004/0225338 A1 | 11/2004 | Lebel et al. |
| 2004/0236200 A1 | 11/2004 | Say et al. |
| 2004/0248204 A1 | 12/2004 | Moerman |
| 2004/0249250 A1 | 12/2004 | McGee et al. |
| 2004/0249253 A1 | 12/2004 | Racchini et al. |
| 2004/0249254 A1 | 12/2004 | Racchini et al. |
| 2004/0249999 A1 | 12/2004 | Connolly et al. |
| 2004/0253736 A1 | 12/2004 | Stout et al. |
| 2004/0254429 A1 | 12/2004 | Yang |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0264396 A1 | 12/2004 | Ginzburg et al. |
| 2005/0003470 A1 | 1/2005 | Nelson et al. |
| 2005/0009126 A1 | 1/2005 | Andrews et al. |
| 2005/0010269 A1 | 1/2005 | Lebel et al. |
| 2005/0016276 A1 | 1/2005 | Guan et al. |
| 2005/0027179 A1 | 2/2005 | Berner et al. |
| 2005/0027180 A1 | 2/2005 | Goode, Jr. et al. |
| 2005/0027181 A1 | 2/2005 | Goode, Jr. et al. |
| 2005/0027462 A1 | 2/2005 | Goode, Jr. et al. |
| 2005/0027463 A1 | 2/2005 | Goode, Jr. et al. |
| 2005/0031689 A1 | 2/2005 | Shults et al. |
| 2005/0033132 A1 | 2/2005 | Shults et al. |
| 2005/0038680 A1 | 2/2005 | McMahon |
| 2005/0043598 A1 | 2/2005 | Goode, Jr. et al. |
| 2005/0043894 A1 | 2/2005 | Fernandez |
| 2005/0045476 A1 | 3/2005 | Neel et al. |
| 2005/0049473 A1 | 3/2005 | Desai et al. |
| 2005/0051580 A1 | 3/2005 | Ramey |
| 2005/0053365 A1 | 3/2005 | Adams et al. |
| 2005/0054909 A1 | 3/2005 | Petisce et al. |
| 2005/0059926 A1 | 3/2005 | Sage, Jr. et al. |
| 2005/0065464 A1 | 3/2005 | Talbot et al. |
| 2005/0090607 A1 | 4/2005 | Tapsak et al. |
| 2005/0090808 A1 | 4/2005 | Malave et al. |
| 2005/0112169 A1 | 5/2005 | Brauker et al. |
| 2005/0113657 A1 | 5/2005 | Alarcon et al. |
| 2005/0113658 A1 | 5/2005 | Jacobson et al. |
| 2005/0118726 A1 | 6/2005 | Scultz et al. |
| 2005/0121322 A1 | 6/2005 | Say et al. |
| 2005/0124873 A1 | 6/2005 | Shults et al. |
| 2005/0137471 A1 | 6/2005 | Haar et al. |
| 2005/0143635 A1 | 6/2005 | Kamath et al. |
| 2005/0143636 A1 | 6/2005 | Zhang et al. |
| 2005/0148003 A1 | 7/2005 | Keith et al. |
| 2005/0154271 A1 | 7/2005 | Rasdal et al. |
| 2005/0161346 A1 | 7/2005 | Simpson et al. |
| 2005/0171503 A1 | 8/2005 | Van Den Berghe et al. |
| 2005/0171512 A1 | 8/2005 | Flaherty |
| 2005/0171513 A1 | 8/2005 | Mann et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0182306 A1 | 8/2005 | Sloan |
| 2005/0182366 A1 | 8/2005 | Vogt et al. |
| 2005/0182451 A1 | 8/2005 | Griffin et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0199494 A1 | 9/2005 | Say et al. |
| 2005/0203360 A1 | 9/2005 | Brauker et al. |
| 2005/0203461 A1 | 9/2005 | Flaherty et al. |
| 2005/0214892 A1 | 9/2005 | Kovatchev et al. |
| 2005/0215871 A1 | 9/2005 | Feldman et al. |
| 2005/0215872 A1 | 9/2005 | Berner et al. |
| 2005/0235732 A1 | 10/2005 | Rush |
| 2005/0238503 A1 | 10/2005 | Rush et al. |
| 2005/0238507 A1 | 10/2005 | DiIanni et al. |
| 2005/0239154 A1 | 10/2005 | Feldman et al. |
| 2005/0239518 A1 | 10/2005 | D'Agostino et al. |
| 2005/0245795 A1 | 11/2005 | Goode, Jr. et al. |
| 2005/0245799 A1 | 11/2005 | Brauker et al. |
| 2005/0249506 A1 | 11/2005 | Fuse |
| 2005/0249606 A1 | 11/2005 | Rush |
| 2005/0251083 A1 | 11/2005 | Carr-Brendel et al. |
| 2005/0261660 A1 | 11/2005 | Choi |
| 2005/0267550 A1 | 12/2005 | Hess et al. |
| 2005/0267780 A1 | 12/2005 | Ray et al. |
| 2005/0271546 A1 | 12/2005 | Gerber et al. |
| 2005/0271547 A1 | 12/2005 | Gerber et al. |
| 2005/0272640 A1 | 12/2005 | Doyle, III et al. |
| 2005/0272985 A1 | 12/2005 | Kotulla et al. |
| 2005/0277844 A1 | 12/2005 | Strother et al. |
| 2005/0287620 A1 | 12/2005 | Heller et al. |
| 2006/0001538 A1 | 1/2006 | Kraft et al. |
| 2006/0001550 A1 | 1/2006 | Mann et al. |
| 2006/0001551 A1 | 1/2006 | Kraft et al. |
| 2006/0003398 A1 | 1/2006 | Heller et al. |
| 2006/0004271 A1 | 1/2006 | Peyser et al. |
| 2006/0007017 A1 | 1/2006 | Mann et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |

(56) References Cited

U.S. PATENT DOCUMENTS

| | | |
|---|---|---|
| 2006/0025663 A1 | 2/2006 | Talbot et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0036187 A1 | 2/2006 | Vos et al. |
| 2006/0040402 A1 | 2/2006 | Brauker et al. |
| 2006/0041229 A1 | 2/2006 | Garibotto et al. |
| 2006/0052679 A1 | 3/2006 | Kotulla et al. |
| 2006/0058602 A1 | 3/2006 | Kwiatkowski et al. |
| 2006/0058627 A1 | 3/2006 | Flaherty et al. |
| 2006/0063218 A1 | 3/2006 | Bartkowiak et al. |
| 2006/0074564 A1 | 4/2006 | Bartkowiak et al. |
| 2006/0094986 A1 | 5/2006 | Neel et al. |
| 2006/0161078 A1 | 7/2006 | Schraga |
| 2006/0166629 A1 | 7/2006 | Reggiardo |
| 2006/0173259 A1 | 8/2006 | Flaherty et al. |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0240403 A1 | 10/2006 | List et al. |
| 2006/0247508 A1 | 11/2006 | Fennell |
| 2006/0253085 A1 | 11/2006 | Geismar et al. |
| 2006/0273759 A1 | 12/2006 | Reggiardo |
| 2006/0282290 A1 | 12/2006 | Flaherty et al. |
| 2007/0016381 A1 | 1/2007 | Kamath et al. |
| 2007/0078314 A1 | 4/2007 | Grounsell et al. |
| 2007/0078323 A1 | 4/2007 | Reggiardo et al. |
| 2007/0106135 A1 | 5/2007 | Sloan |
| 2007/0118405 A1 | 5/2007 | Campbell et al. |
| 2007/0135697 A1 | 6/2007 | Reggiardo |
| 2007/0163880 A1 | 7/2007 | Woo et al. |
| 2007/0173711 A1 | 7/2007 | Shah et al. |
| 2007/0173761 A1 | 7/2007 | Kanderian, Jr. et al. |
| 2007/0176867 A1 | 8/2007 | Reggiardo et al. |
| 2007/0203966 A1 | 8/2007 | Brauker et al. |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2007/0282299 A1 | 12/2007 | Hellwig |
| 2008/0021666 A1 | 1/2008 | Goode, Jr. et al. |
| 2008/0033254 A1 | 2/2008 | Kamath et al. |
| 2008/0045824 A1 | 2/2008 | Tapsak et al. |
| 2008/0064941 A1 | 3/2008 | Funderburk et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0103447 A1 | 5/2008 | Reggiardo et al. |
| 2008/0108942 A1 | 5/2008 | Brister et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200838 A1 | 8/2008 | Goldberger et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0006133 A1 | 1/2009 | Weinert et al. |
| 2009/0012379 A1 | 1/2009 | Goode et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0062633 A1 | 3/2009 | Brauker et al. |
| 2009/0062635 A1 | 3/2009 | Brauker et al. |
| 2009/0063402 A1 | 3/2009 | Hayter |
| 2009/0068954 A1 | 3/2009 | Reggiardo et al. |
| 2009/0076356 A1 | 3/2009 | Simpson et al. |
| 2009/0076358 A1 | 3/2009 | Reggiardo et al. |
| 2009/0076360 A1 | 3/2009 | Brister et al. |
| 2009/0076361 A1 | 3/2009 | Kamath et al. |
| 2009/0083003 A1 | 3/2009 | Reggiardo et al. |
| 2009/0099436 A1 | 4/2009 | Brister et al. |
| 2009/0105560 A1 | 4/2009 | Solomon |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0253973 A1 | 10/2009 | Bashan et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |

(56) References Cited

U.S. PATENT DOCUMENTS

| | | |
|---|---|---|
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |
| 2010/0198196 A1 | 8/2010 | Wei |
| 2010/0312176 A1 | 12/2010 | Lauer et al. |

FOREIGN PATENT DOCUMENTS

| | | |
|---|---|---|
| CA | 2498682 | 9/2005 |
| CA | 2555749 | 9/2005 |
| CA | 2632709 | 6/2007 |
| CA | 2615575 | 6/2008 |
| CA | 2701374 | 4/2009 |
| EP | 0455455 | 11/1991 |
| EP | 0518524 | 12/1992 |
| EP | 0878707 | 11/1998 |
| EP | 0543916 | 7/2001 |
| EP | 1130638 | 9/2001 |
| EP | 1755443 | 11/2005 |
| EP | 1783536 | 5/2007 |
| EP | 1956371 | 8/2008 |
| EP | 2260757 | 12/2010 |
| JP | 2001-177423 | 6/2001 |
| JP | 2001-056673 | 11/2001 |
| WO | WO-96/14026 | 5/1996 |
| WO | WO-99/22236 | 5/1999 |
| WO | WO-01/52727 | 7/2001 |
| WO | WO-01/71186 | 9/2001 |
| WO | WO-02/39086 | 5/2002 |
| WO | WO-02/084860 | 10/2002 |
| WO | WO-02/100263 | 12/2002 |
| WO | WO-02/100469 | 12/2002 |
| WO | WO-03/006091 | 1/2003 |
| WO | WO-2004/015539 | 2/2004 |
| WO | WO-2004/028337 | 4/2004 |
| WO | WO-2004/032994 | 4/2004 |
| WO | WO-2004/061420 | 7/2004 |
| WO | WO-2005/089103 | 9/2005 |
| WO | WO-2005/101994 | 11/2005 |
| WO | WO-2006/003919 | 1/2006 |
| WO | WO-2006/079114 | 7/2006 |
| WO | WO-2006/086701 | 8/2006 |
| WO | WO-2006/102412 | 9/2006 |
| WO | WO-2006/110913 | 10/2006 |
| WO | WO-2006/113408 | 10/2006 |
| WO | WO-2006/113521 | 10/2006 |
| WO | WO-2006/118947 | 11/2006 |
| WO | WO-2006/132884 | 12/2006 |
| WO | WO-2007/041072 | 4/2007 |
| WO | WO-2007/065285 | 6/2007 |
| WO | WO-2007/090037 | 8/2007 |
| WO | WO-2007/149319 | 12/2007 |
| WO | WO-2008/001366 | 1/2008 |
| WO | WO-2008/055037 | 5/2008 |
| WO | WO-2008/110267 | 9/2008 |
| WO | WO-2008/151452 | 12/2008 |
| WO | WO-2009/049252 | 4/2009 |
| WO | WO-2011/104616 | 9/2011 |

OTHER PUBLICATIONS

Barbosa, R. M., et al., "Electrochemical Studies of Zinc in Zinc-Insulin Solution", *Journal of the Royal Society of Chemistry, Analyst*, vol. 121, No. 12, 1996, pp. 1789-1793.

Bard, A. J., et al., "Methods Involving Forced Convection—Hydrodynamic Methods", *Electrochemical Methods—Fundamentals and Applications*, 2001, pp. 331-367.

Kissinger, P. T., "Introduction to Analog Instrumentation", *Laboratory Techniques in Electroanalytical Chemistry, Second Edition, Revised and Expanded*, 1996, pp. 165-194.

Ursino, M, et al., "A Mathematical Model of Cerebral Blood Flow Chemical Regulation—Part I: Diffusion Processes", *IEEE Transactions on Biomedical Engineering*, vol. 36, No. 2, 1989, pp. 183-191.

COMPUTERIZED DETERMINATION OF INSULIN PUMP THERAPY PARAMETERS USING REAL TIME AND RETROSPECTIVE DATA PROCESSING

BACKGROUND

Diabetic patients typically administer insulin to sustain their physiological conditions. Typically, these patients administer doses of either fast acting or slow acting insulin using needle type syringes, for example, prior to meals, and/or at a suitable time during the course of each day contemporaneously with the blood glucose level testing using fingerstick blood glucose testing, for example. If insulin is not suitably administered, the diabetic patients risk serious if not fatal damage to the body.

Continued development and improvement in the external infusion pump therapy in recent years have drawn much appeal to the diabetic patients for, among others, improved management of diabetes by better regulating and controlling the intake of insulin. Typically, the patient inserts a cannula which is connected to as infusion tubing attached to an external pump, and insulin is administered based on a preprogrammed basal profiles. Moreover, the external infusion devices presently available include computational capability to determined suitable bolus doses such as carbohydrate bolus and correction bolus, for example, to be administered in conjunction with the infusion device executing the patient's basal profile.

Commercially available infusion devices such as insulin pumps are programmable and include sophisticated functionalities to enhance therapy management. Consistent with the sophistication of these devices, it is often cumbersome and trying to program these complex devices to the desired delivery, notification, modification and/or other adjustments or settings to be suitable for each user's physiology or therapy.

Programming such infusion devices require the entry of many variables and parameters, some of which are entered or provided into the device based, at least in part on the knowledge or experience of the user and/or the healthcare provider. For example, to modify one or more basal delivery settings, the infusion device user may use prior knowledge based on past experience, in addition to subjectively determined parameters, for example, the time period for inputting measurement values of the blood glucose level when determining a correction bolus amount.

It goes without saying for diabetics on insulin pump therapy, continual refinement of the basal insulin delivery rate, insulin to carbohydrate ratio determination, insulin sensitivity level, duration of insulin action, to name a few, are important in achieving successful therapy management. Often times, however, the refinement process is complex and iterative.

SUMMARY

Embodiments of the subject disclosure include methods device for programming a therapy delivery device such as a medication infusion device including, for example insulin pump. More particularly, embodiments of the present disclosure include receiving a respective data set from an infusion device and an analyte monitoring device for a predetermined time duration, time synchronizing the received respective data set, detecting one or more marked data from the one or more respective data set received, performing automated data analysis based on the detected one or more marked data or data filters to generate a modification to a therapy profile, and providing the generated modification to the therapy profile.

Also provided are systems, computer program products, and kits.

BRIEF DESCRIPTION OF THE DRAWINGS

FIGS. 3-14 are screen shot illustrations of the overall computerized adjustment to therapy parameters using real time and retrospective data processing in accordance with one aspect of the present disclosure.

DETAILED DESCRIPTION

Figure 1:
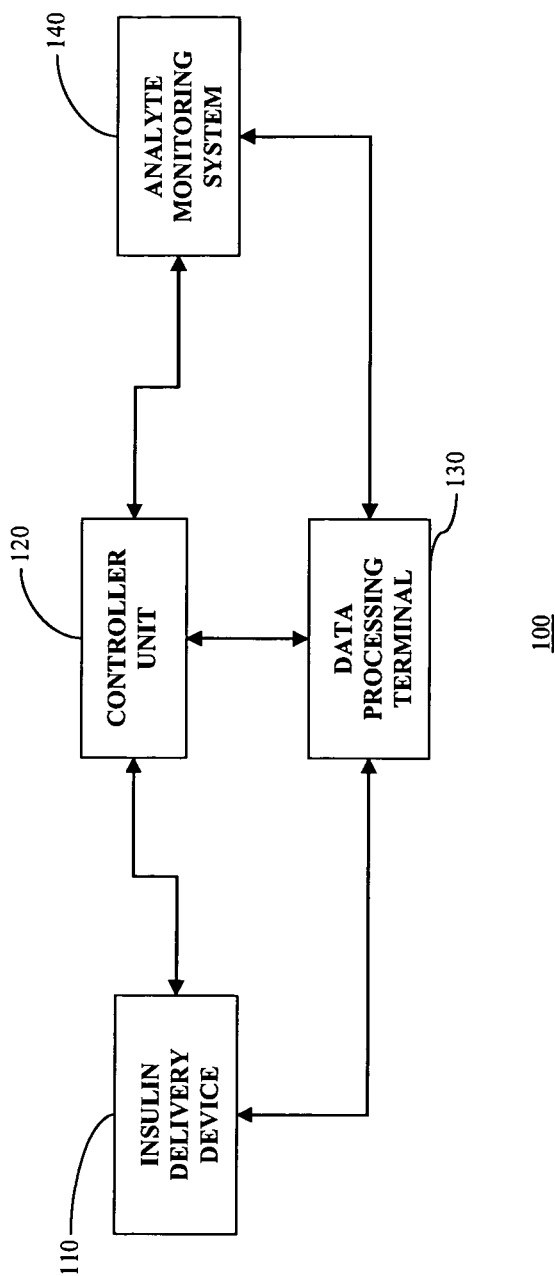
FIG. 1 shows a block diagram of an overall computerized adjustment to therapy parameters using real time and retrospective data processing in accordance with one aspect.

Within the scope of the present disclosure, there are provided method and system for providing automated or semi-automated computerized adjustment to therapy parameters using real time and retrospective data processing including device and/data synchronization, bi-directional communication, data storage and processing, as well as providing a robust user interface. Embodiments of the present disclosure include predetermined time period for data collection including data related to monitored analyte levels, infusion device delivery characteristics, and events markers, if any associated with the user. Upon expiration of the data collection period, the information is uploaded to a data management and analysis tool which, in one embodiment, may be configured to automatically initiate processing of the received data, including, detecting data marked or identified for performing automatic or semi-automatic adjustment, and output or generate a recommended refinement to the therapy profile, for example, which is then output to the user or the healthcare provider or directly programmed into the therapy delivery device.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

FIG. 1 shows a block diagram of an overall therapy delivery device programming tool in accordance with one aspect of the present disclosure. Referring to the Figure, the system for providing automated or semi-automated computerized adjustment to therapy parameters using real time and retrospective data processing 100 includes a therapy delivery device 110 such as an insulin delivery device capable of data communication with a controller unit 120 and a data processing terminal 130. Also shown in an analyte monitoring system 140 configured for communication with the controller unit 120 and the data processing terminal 130. In aspects of the present disclosure, the analyte monitoring system 140 may be configured to communicate directly with the therapy delivery device 110.

Within the scope of the present disclosure, two or more of the components shown in the system 100 of FIG. 1 may be integrated into a single device or housing. For example, the insulin delivery device 110 and the analyte monitoring system 140 may be provided in a single integrated device housing while maintaining the separate functionality of medication delivery and analyte monitoring, respectively.

The therapy delivery device 110 in one embodiment may include an external infusion device such as an external insulin pump, an implantable infusion device, an on-body micropump device, a transdermal delivery device, or any other suitable microprocessor controlled medication delivery device. Furthermore, the analyte monitoring system 140 may include, one or more transcutaneous analyte sensors such as glucose sensors configured for fluid contact with an analyte of a user for a predetermined time period such as for example, approximately five days, seven days or more.

Referring back to FIG. 1, the controller unit 120 may be configured in one aspect to perform some or all of the control functions associated with the operation of the insulin delivery device 110 and/or the analyte monitoring system 140. In another aspect, the control functions and operations provided to the controller unit 120 may be to provide redundancy in operation, such that the same operations and/or control functions may be provided in the respective insulin delivery device 110 and/or the analyte monitoring system 140.

In one aspect, the therapy delivery device 110 may include one or more user interface components such as a display, input buttons, speakers for providing audible or audio output, and the like. In one aspect, the therapy delivery device 110 may be an ambulatory device and configured to be carried around by the user. In still a further aspect, the therapy delivery device 110 may include a communication component which allows the device 110 to connect to or communicate with one or more of the controller unit 120 and the data processing terminal 130. The communication link between the therapy delivery device 110 and the one or more of the controller unit 120 and the data processing terminal 130 may include RF communication, Infrared communication, 801.x1 based communication protocol, cellular network based communication protocol and the like. In accordance with aspects of the present disclosure, the communication between the various components of the overall system 100 shown in FIG. 1 may also includes wires connection using, for example, USB connection, RS-232 connection, or any other suitable data transfer connection.

In one aspect, the therapy delivery device 110 may be configured to deliver medication such as insulin using an infusion set connectable to the housing of the device and in fluid communication with one or more reservoirs housed within the device 110, where the infusion set includes a cannula for medication delivery to the user or patient. In a further aspect, the therapy delivery device 110 is microprocessor driven and controlled by one or more microprocessor units to execute functions related to the medication delivery, operational condition monitoring of the therapy delivery device, and the like.

Referring back to FIG. 1, also shown is the controller unit 120 which may include a wireless or wired communication device which is configured to control at least in part, the operation of the therapy delivery device, and further, configured to communicate with the data processing terminal 130. Each communication link between the various components shown in FIG. 1 including the therapy delivery device 110, the controller unit 120, and the data processing terminal 130 may be bidirectional. In one aspect, the controller unit 120 may include some or all of the functionalities provided in the therapy delivery device 110 including the control of the medication dispensing protocol, condition notification such as detected occlusion in the infusion tubing, and/or along the fluid path from the therapy delivery device 110 to the user, programming, controlling or monitoring the operation of the therapy delivery device 110.

Optionally, the controller unit 120 may include a strip port for receiving an in vitro blood glucose test strip for determining a blood glucose measurement. Additionally, the controller unit 120 may include the functionalities of an analyte monitoring device which may be configured to be in communication with an analyte sensor for monitoring an analyte level of a user. Further detailed descriptions of embodiments of the continuous analyte monitoring system, embodiments of its various components are provided in U.S. Pat. No. 6,175,752 issued Jan. 16, 2001 entitled "Analyte Monitoring Device and Methods of Use", and in application Ser. No. 10/745,878 filed Dec. 26, 2003 entitled "Continuous Glucose Monitoring System and Methods of Use", each assigned to the Assignee of the present application, disclosure of each of which are incorporated by reference for all purposes.

Referring back to FIG. 1, the data processing terminal 130 in one aspect may include a personal computer, a portable computer such as a laptop or a handheld device (e.g., personal digital assistants (PDAs), telephones such as a cellular phones (e.g., a multimedia and Internet-enabled mobile phone such as an iPhone or a Blackberry device), mp3 players, pagers, and the like), each of which may be configured for data communication with the delivery device 110 and/or the controller unit 120 via wired or wireless connection. Additionally, the data processing terminal 130 may further be connected to a data network (not shown) for storing, retrieving, updating, and/or analyzing data associated with the therapy delivery device 110 as well as the controller unit 120.

In this manner, in accordance with aspects of the present disclosure, data collected or monitored by the insulin delivery device 110, the controller unit 120 and/or the analyte monitoring system 140 is provided to the data processing terminal 130 which in turn, may be configured to perform, automatically or semi-automatically, processing of the collected and received data, to modify the therapy management profile to recommend to the user and for execution by the insulin delivery 110 to improve glycemic control. That is, in one aspect, the data processing terminal 130 may be configured to include software or programming to receive data associated with insulin delivery and time corresponding monitored analyte levels from the delivery device 110 and the analyte monitoring system 140, respectively, and automatically or semi-automatically, with one or more user inputs or prompts, execute data analysis and therapy recommendation procedure or routine.

Figure 2:
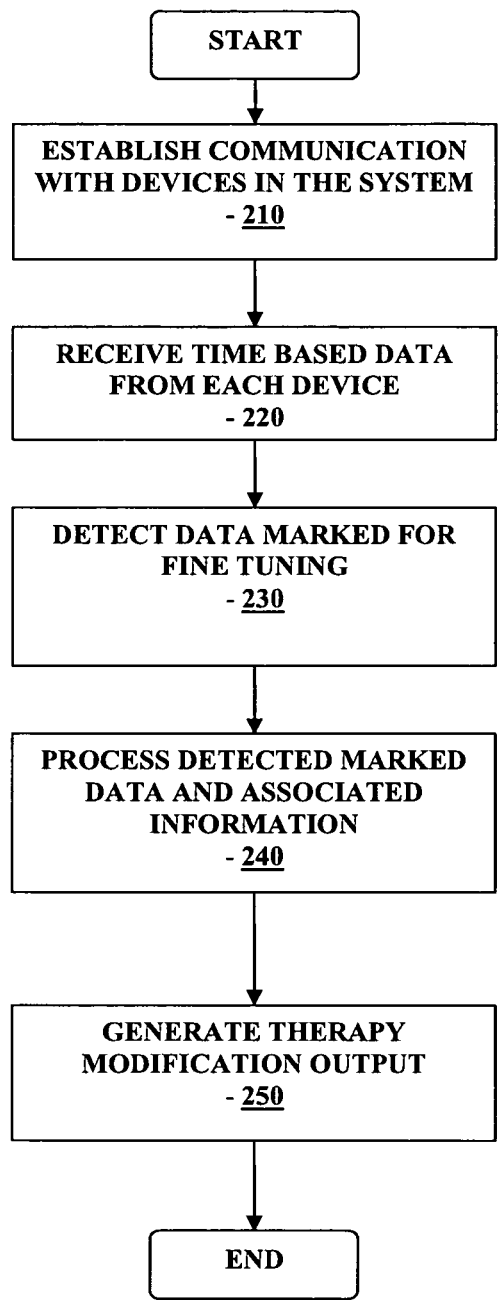
FIG. 2 is a flowchart illustrating a routine for computerized adjustment to therapy parameters using real time and retrospective data processing in accordance with one aspect of the present disclosure.

FIG. 2 is a flowchart illustrating a routine for computerized adjustment to therapy parameters using real time and retrospective data processing in accordance with one aspect of the present disclosure. Referring to the Figure, after a predetermined time has elapsed, the data processing terminal 130 may be configured to initiate communication with the devices in the overall system including, for example insulin delivery device 110, the controller unit 120 and the analyte monitoring system 140 (210). The predetermined time period may be programmable and based on, for example, a time window that is sufficiently wide to provide meaningful data for analysis and processing to determine fine tuning of the therapy profile or patient achieving certain targeted events as prescribed by the physician.

In one aspect, the communication between the data processing terminal 130 and the devices in the system 100 may not be initiated by the data processing terminal 140, but rather, established at different time periods when each of the insulin delivery device 110, the controller unit 120 and the analyte monitoring system 140 is within communication range with the data processing terminal 140, and which may include overlapping but not identical time periods for each communication from the various devices to the data processing terminal 140. In such as case, it is important to have the clocks or timing components in each device in the system 100 to be synchronized, such that the data processing terminal 130 may accurately correlate the information received from each device. That is, the time base for data or information from each device in the system may be synchronized to provide meaningful and accurate data.

Referring to FIG. 2, with the communication link established, the time based data from each device is received or collected for example, representative of the time period or predetermined time period identified by the data processing terminal 130 (FIG. 1) for analysis (220). The data processing terminal 130 may be further configured to detect data marked for fining tuning (230) based on preliminary analysis of information received from each device. For example, instances of hypoglycemia and/or hyperglycemia detection from the analyte monitoring system 140, ingesting of prescribed meal and its impact on the subsequent detected rate of change of the analyte level, detected rate of change of the analyte levels that deviate beyond a predefined level of tolerance, and the like, which events are correspondingly marked by the respective devices such as the analyte monitoring system 140 and identified as part of the data transfer from the analyte monitoring system 140 to the data processing terminal 130.

Similarly, data from the insulin delivery device 110 may be marked by the device during the course of the medication delivery, and thereafter provided to the data processing terminal 130. Examples of such marked data may include, but is not limited to, time information associated with user administered bolus doses, execution of temporary basal and delivery profiles for the same, bolus insulin amount and its impact on the subsequent rate of change of analyte level, compliance or noncompliance to alarm or alert conditions, and the like. In one aspect, the insulin delivery device 110 may be programmed to detect occurrence of such event and identify data or information associated with the detection of such occurrences and subsequently to provide that information in addition to the associated data to the data processing terminal 130.

Referring back to FIG. 2, in one aspect, the data processing terminal 130 (FIG. 1) is configured to perform one or more processes or routines to analyze the detected marked data and associated information received from the insulin delivery device 110, the controller unit 120 and the analyte monitoring system 140 (240). After processing the detected marked data and associated information, the data processing terminal 130 may be configured to generate a therapy modification output that refines or fine tunes the one or more aspect of the therapy management associated with the marked data or unmarked data if they meet certain prescribed filtering criteria (250). In one aspect, the generated therapy modification as well as the underlying processing may be performed automatically by the data processing terminal 130 upon detection of the communication link with the one or more devices in the system 100. Alternatively, within the scope of the present disclosure, the analysis and fine tuning of the therapy profile may be initiated based on user prompt or command, or upon detection of a predetermined time period for which data from the various devices and components have been received so as to provide a meaningful analysis based on marked data and associated information.

Figure 3:
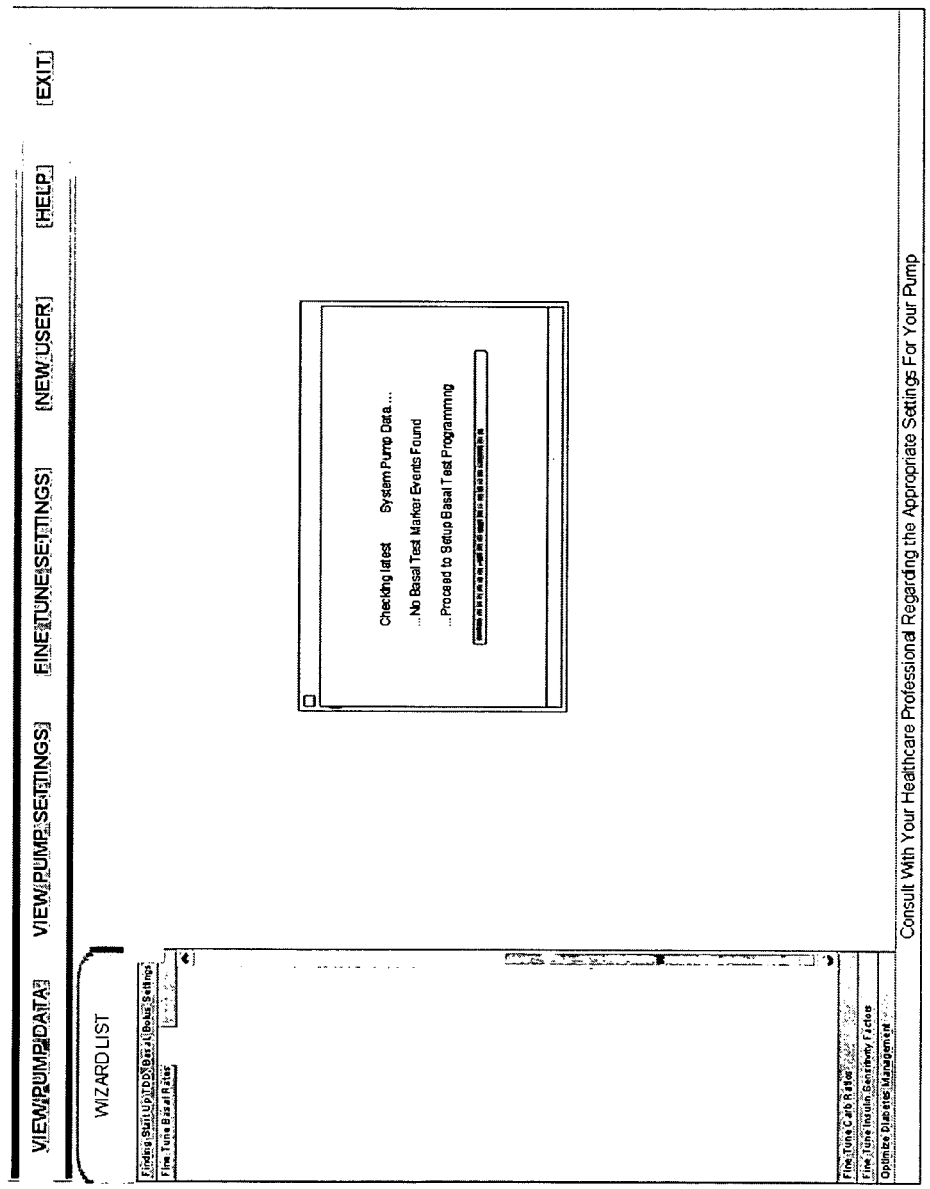
Figure 4:
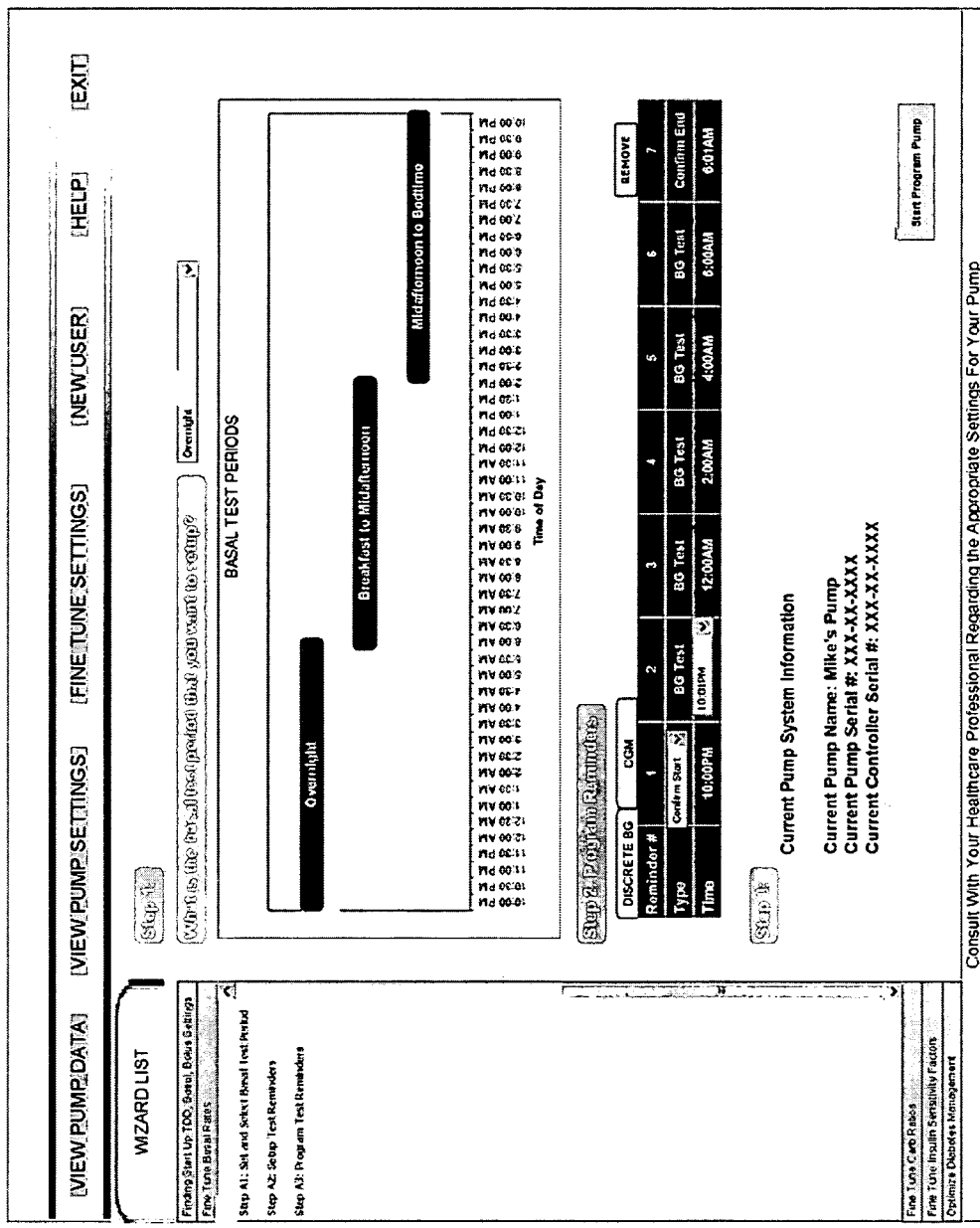
Figure 6:
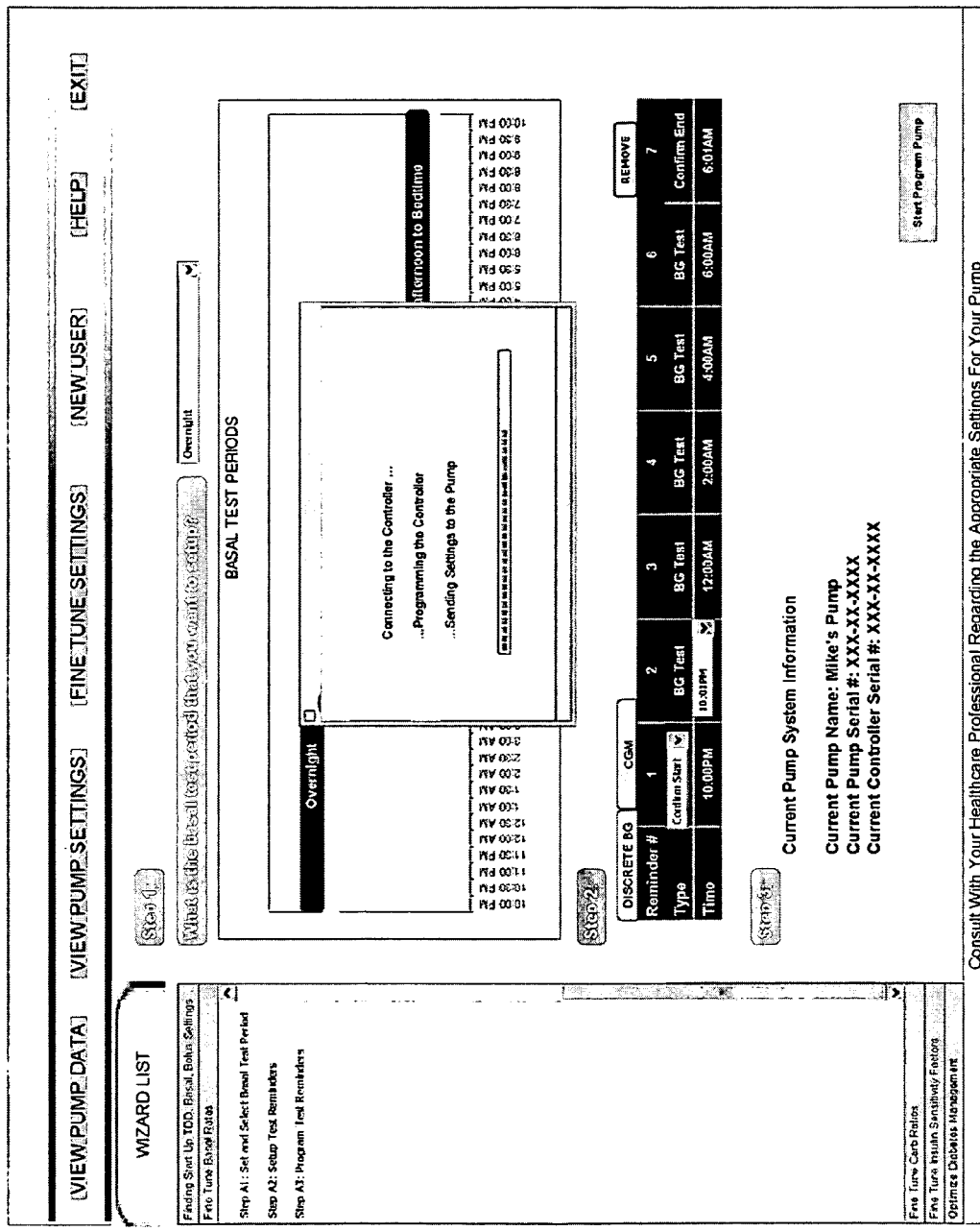
Figure 7:
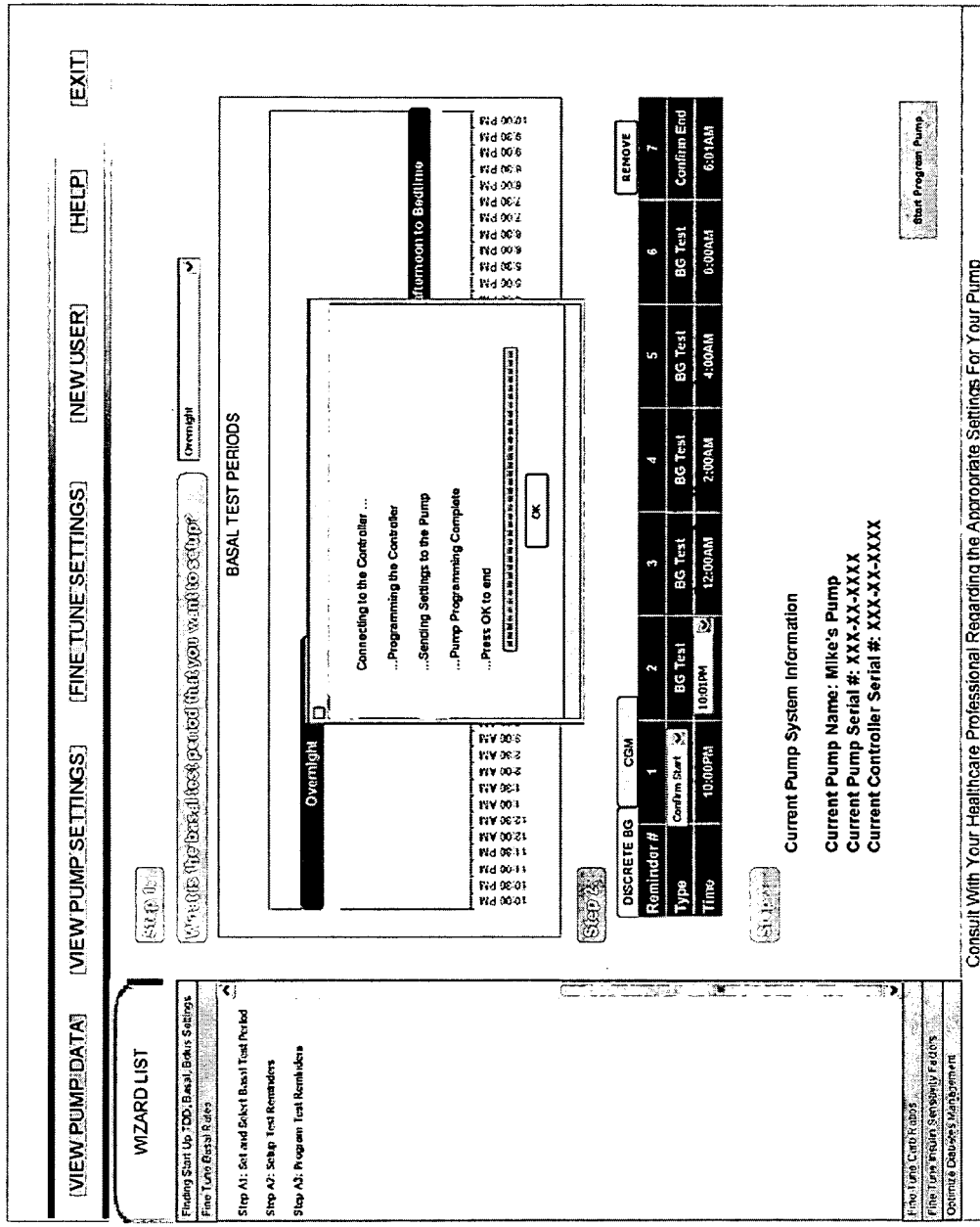
Figure 8:
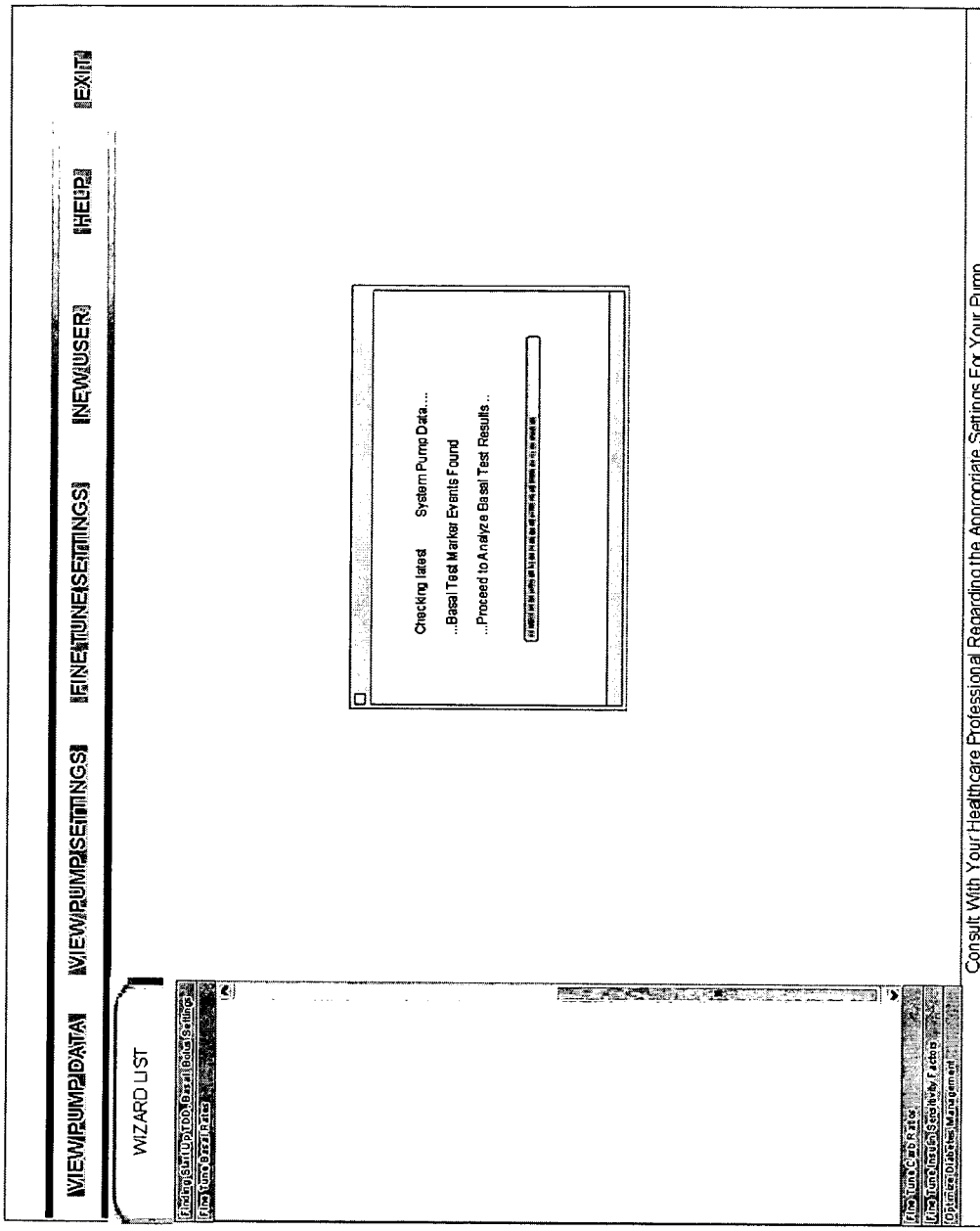
Figure 9:
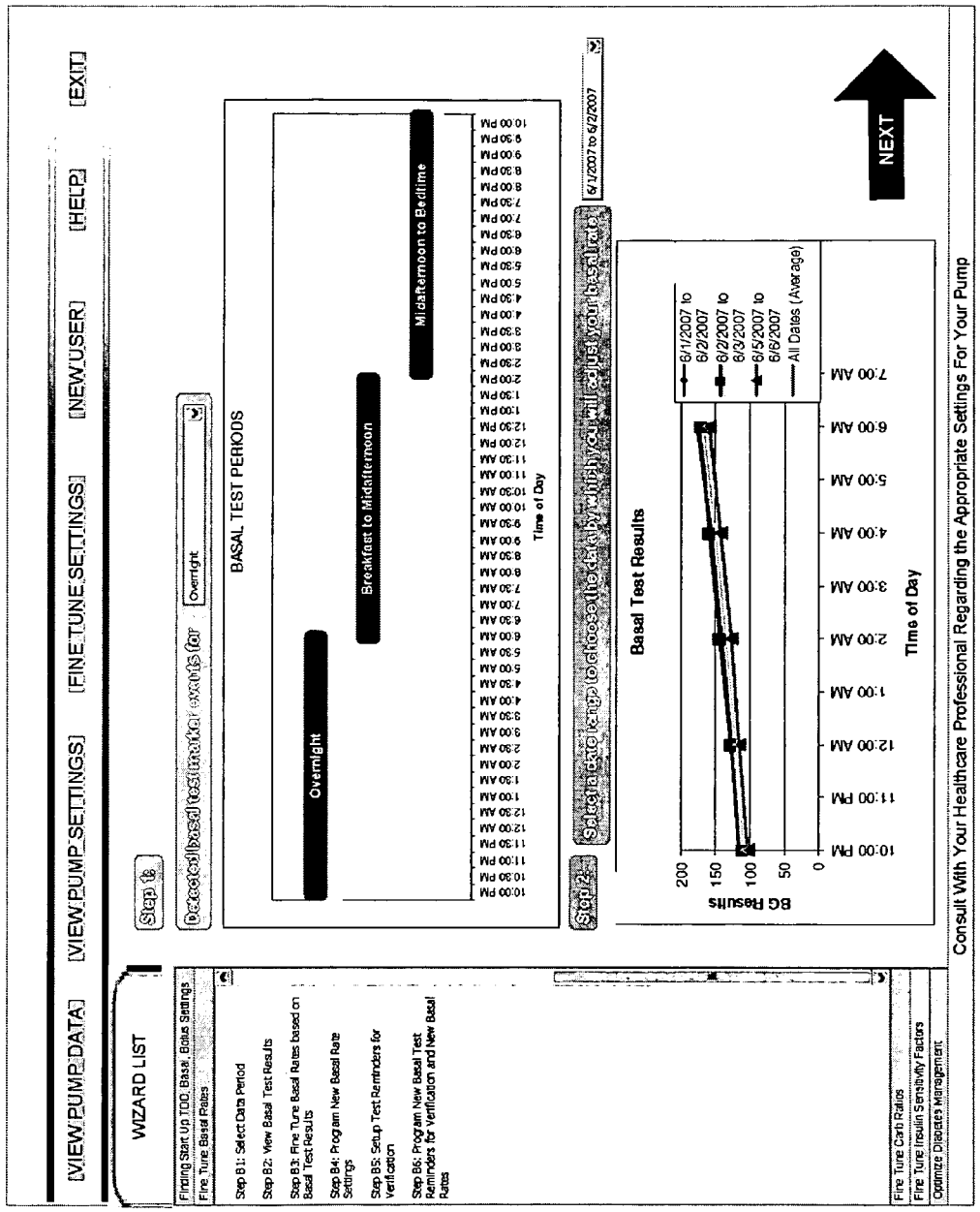
Figure 10:
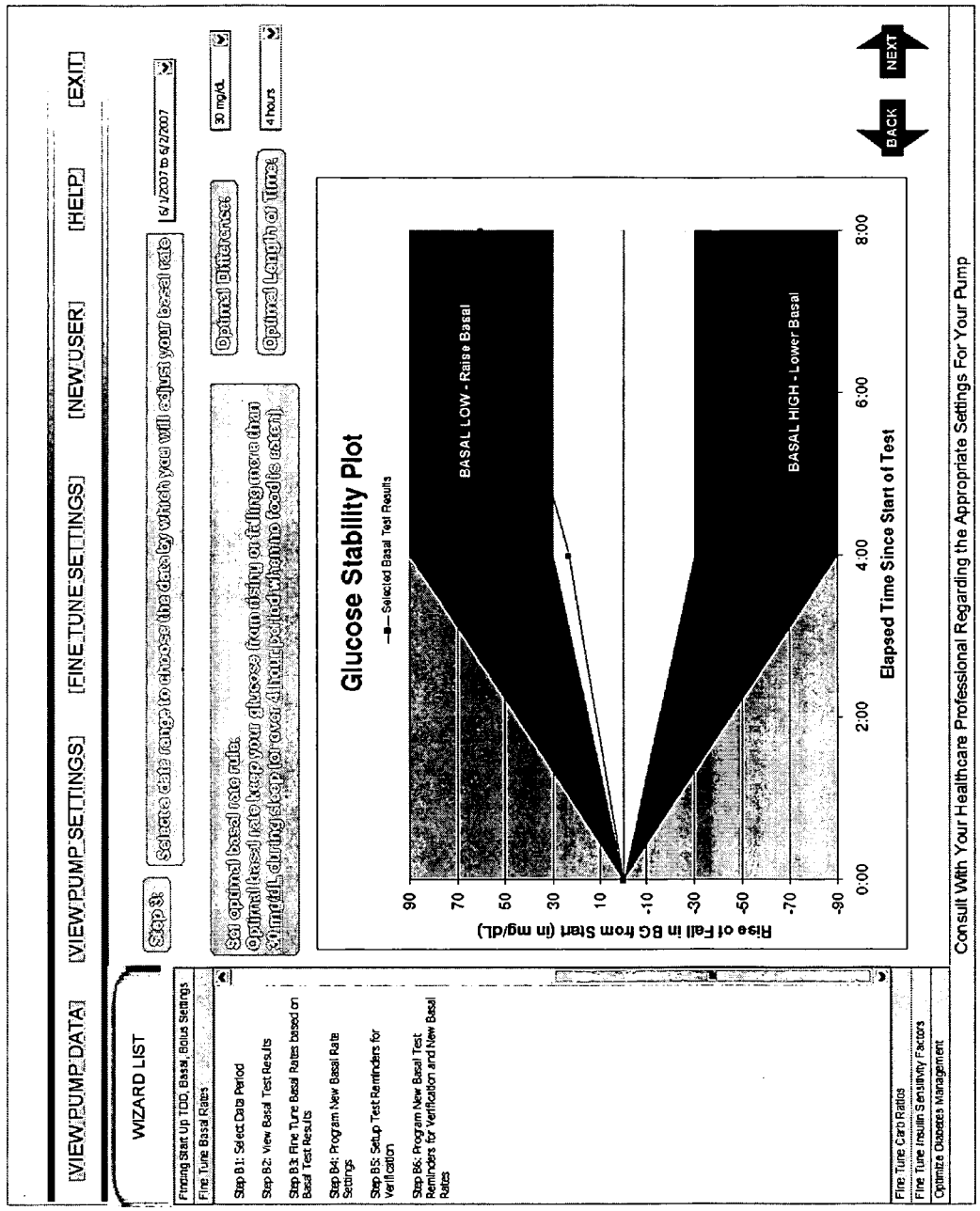
Figure 12:
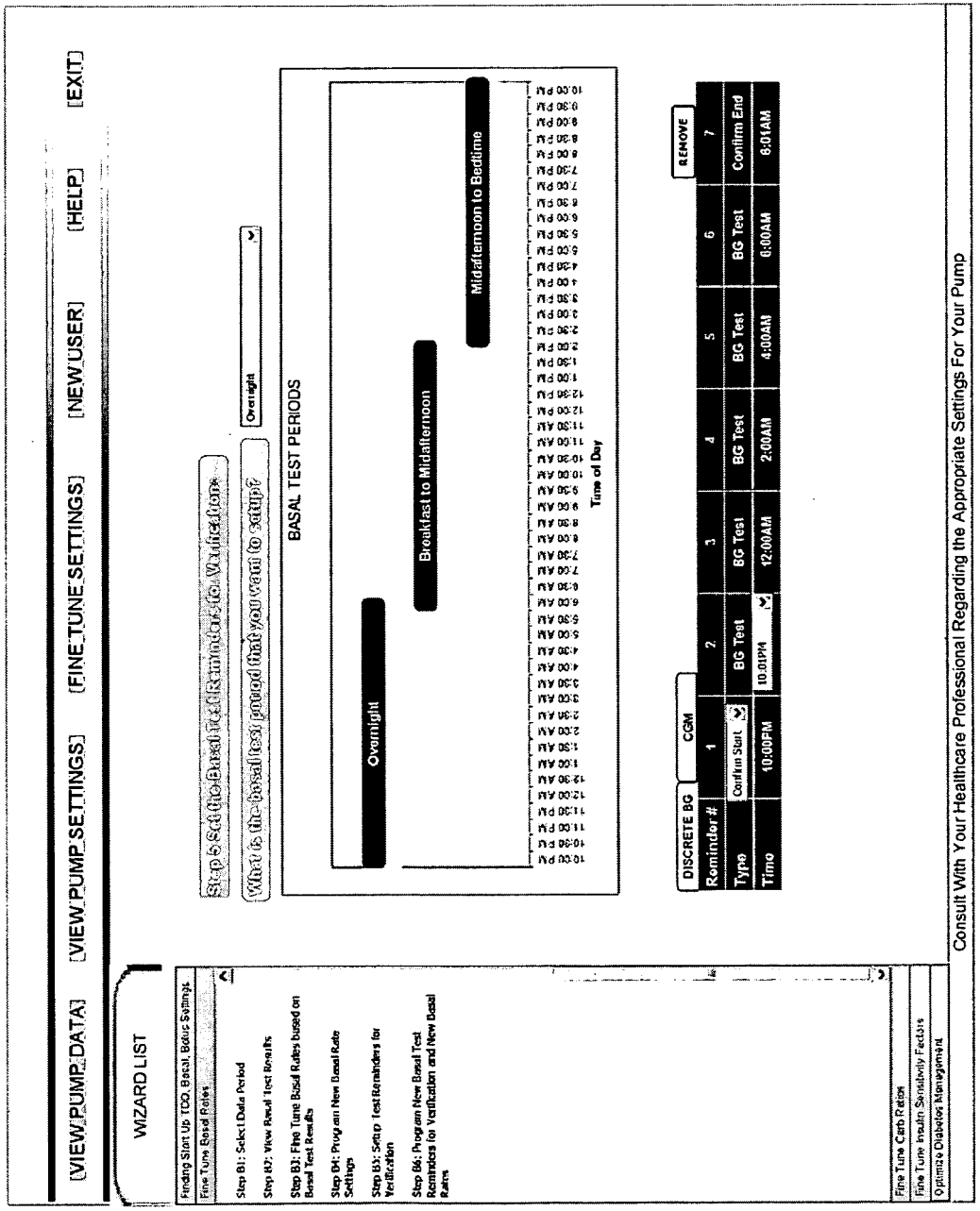

FIGS. 3-14 are screen shot illustrations of the overall computerized adjustment to therapy parameters using real time and retrospective data processing in accordance with one aspect of the present disclosure. As shown in the Figures, during data connection and processing, the status information as well as user inputtable parameters are displayed in one embodiment as visual representation to the user. For example, FIG. 3 shows a status screen during data collection or synchronization with the delivery device 110 including, for example, search and verification of any data marked (for example, the basal test marker events shown). As can be further seen from FIGS. 3-14, during the data collection, synchronization and processing routines, the data processing terminal 130 may be configured to provide a step by step visual presentation of the information being processed and various routines being executed, and optionally request user input or confirmation.

In another aspect, the data processing terminal 130 may be programmed with one or more predefined filter functions and configured to identify relevant segments of retrospective or historical data that can be used for further analysis.

Accordingly, one embodiment of the present disclosure includes receiving a respective data set from an infusion device and an analyte monitoring device for a predetermined time duration, time synchronizing the received respective data set, detecting one or more marked data from the one or more respective data set received, performing automated data analysis based on the detected one or more marked data to generate a modification to a therapy profile, and providing the generated modification to the therapy profile.

The data set from the infusion device includes an executed medication delivery profile associated with the predetermined time duration.

The data set from the analyte monitoring device includes monitored analyte level associated with the predetermined time duration.

Time synchronizing the received respective data set includes aligning the time information of each data set based on a common time base.

In one aspect, the detected one or more marked data includes an indication of a hypoglycemic event, a hypoglycemic event, a rate of change of analyte level exceeding a predetermined threshold level, therapy compliance information, missed analyte sensor calibration event, missed meal bolus event, frequency alarm event, and frequency of alert event.

Further, performing the automated data analysis includes refining an executed therapy profile based at least in part in the data processing associated with the marked data and related information.

Also, in one aspect, the automated data analysis is initiated in response to the detection of the marked data.

Also, in another respect, the automated data analysis may be initiated in response to the data achieving a preset number of prescribed events to proceed with meaningful analyses.

Moreover, in a further aspect, the therapy profile includes insulin therapy profile.

Additionally included in a further embodiment is transmitting the generated modification to the therapy profile in response to a received confirmation.

An apparatus in accordance with another aspect includes a data communication interface, one or more processors operatively coupled to the data communication interface, a memory for storing instructions which, when executed by the one or more processors, causes the one or more processors to receive a respective data set from an infusion device and an analyte monitoring device for a predetermined time duration, time synchronize the received respective data set, detect one or more marked data from the one or more respective data set received, perform automated data analysis based on the detected one or more marked data to generate a modification to a therapy profile, and provide the generated modification to the therapy profile.

Moreover, one or more storage devices having processor readable code embodied thereon, said processor readable code for programming one or more processors to fine tune therapy profile in accordance with still another aspect may include receiving a respective data set from an infusion device and an analyte monitoring device for a predetermined time duration, time synchronizing the received respective data set, detecting one or more marked data from the one or more respective data set received, performing automated data analysis based on the detected one or more marked data to generate a modification to a therapy profile, and providing the generated modification to the therapy profile.

The various processes described above including the processes performed by the delivery device 110, the controller unit 120, the analyte monitoring system 140, and the data processing terminal 130 (FIG. 1) in the software application execution environment in the overall system for providing delivery device programming tool 100 including the processes and routines described in conjunction with FIG. 2, may be embodied as computer programs developed using an object oriented language that allows the modeling of complex systems with modular objects to create abstractions that are representative of real world, physical objects and their interrelationships. The software required to carry out the inventive process, which may be stored in the memory or storage device (not shown) of the delivery device 110, the controller unit 120, the data processing terminal 130, and the analyte monitoring system 140 may be developed by a person of ordinary skill in the art and may include one or more computer program products.

Various other modifications and alterations in the structure and method of operation of this disclosure will be apparent to those skilled in the art without departing from the scope and spirit of the embodiments of the present disclosure. Although the present disclosure has been described in connection with particular embodiments, it should be understood that the present disclosure as claimed should not be unduly limited to such particular embodiments. It is intended that the following claims define the scope of the present disclosure and that structures and methods within the scope of these claims and their equivalents be covered thereby.

What is claimed is:

1. A method, comprising:
receiving a respective data set from an infusion device and an analyte monitoring device for a predetermined time duration;
time synchronizing the received respective data set;
detecting one or more marked data from the one or more respective data set received;
performing automated data analysis based on the detected one or more marked data to generate a modification to a therapy profile; and
providing the generated modification to the therapy profile.

2. The method of claim 1 wherein the data set from the infusion device includes an executed medication delivery profile associated with the predetermined time duration.

3. The method of claim 1 wherein the infusion device is configured to notify a user that the predetermined time duration is in effect.

4. The method of claim 1 including performing the automated data analysis based on detection of the occurrence of a preset number of events and/or conditions in the respective data set to generate the modification to the therapy profile.

5. The method of claim 4 including providing user formulation tools to modify one or more rules or guidelines for therapy modification.

6. The method of claim 1 wherein the data set from the analyte monitoring device includes monitored analyte level associated with the predetermined time duration.

7. The method of claim 1 wherein the analyte monitoring device is configured to notify a user that the predetermined time duration is in effect.

8. The method of claim 1 wherein time synchronizing the received respective data set includes aligning a time of event occurrence information for associated events of each data set based on a common time base.

9. The method of claim 1 wherein the detected one or more marked data includes an indication of a meal event, exercise event, drug ingestion event, health state event, hypoglycemic event, hyperglycemic event, rate of change of analyte level exceeding a predetermined threshold level, therapy compliance information, missed analyte sensor calibration event, missed meal bolus event, frequency alarm event, and frequency of alert event.

10. The method of claim 1 wherein performing the automated data analysis includes refining an executed therapy profile based at least in part in the data processing associated with the marked data and related information.

11. The method of claim 1 wherein performing the automated data analysis includes refining an executed therapy profile based at least in part in the data processing associated with a pre-defined filter criteria of unmarked data.

12. The method of claim 1 wherein the automated data analysis is initiated in response to the detection of the marked data.

13. The method of claim 1 wherein the automated data analysis is initiated in response to the data achieving a preset number of pre-defined events or conditions.

14. The method of claim 1 wherein the therapy profile includes insulin therapy profile, glucose alarm settings, target blood glucose profile, carbohydrate ratio profile or insulin sensitivity profile.

15. The method of claim 1 including transmitting the generated modification to the therapy profile in response to a received confirmation.

16. The method of claim 1 including generating or modifying one or more rules for generating therapy profile modification.

17. An apparatus, comprising:
a data communication interface;
one or more processors operatively coupled to the data communication interface; and
a memory for storing instructions which, when executed by the one or more processors, causes the one or more processors to receive a respective data set from an infusion device and an analyte monitoring device for a predetermined time duration, time synchronize the received respective data set, detect one or more marked data from the one or more respective data set received, perform automated data analysis based on the detected one or more marked data to generate a modification to a therapy profile, and provide the generated modification to the therapy profile.

18. The apparatus of claim 17 wherein the data set from the infusion device includes an executed medication delivery profile associated with the predetermined time duration.

19. The apparatus of claim 17 wherein the memory for storing instructions which, when executed by the one or more processors causes the one or more processors to issue one or more notification to perform or prohibit performance of one or more user based events during the predetermined time period.

20. The apparatus of claim 17 wherein the respective data set received from the analyte monitoring device includes monitored analyte level associated with the predetermined time duration.

21. The apparatus of claim 17 wherein the memory for storing instructions which, when executed by the one or more processors, causes the one or more processors to align the time information of each data set based on a common time base.

22. The apparatus of claim 17 wherein the detected one or more marked data includes an indication of a meal event, exercise event, drug ingestion event, health state event, hypoglycemic event, hyperglycemic event, rate of change of analyte level exceeding a predetermined threshold level, therapy compliance information, missed analyte sensor calibration event, missed meal bolus event, frequency alarm event, and frequency of alert event.

23. The apparatus of claim 17 wherein the memory for storing instructions which, when executed by the one or more processors, causes the one or more processors to refine an executed therapy profile based at least in part in the data processing associated with the marked data and related information.

24. The apparatus of claim 17 wherein the memory for storing instructions which, when executed by the one or more processors, causes the one or more processors to refine an executed therapy profile based at least in part in the data processing associated with a pre-defined filter criteria of unmarked data.

25. The apparatus of claim 17 wherein the automated data analysis is initiated in response to the detection of the marked data.

26. The apparatus of claim 17 wherein the therapy profile includes insulin therapy profile, glucose alarm settings, target blood glucose profile, carbohydrate ratio profile, or insulin sensitivity profile.

27. The apparatus of claim 17 wherein the memory for storing instructions which, when executed by the one or more processors, causes the one or more processors to transmit the generated modification to the therapy profile in response to a received confirmation.

28. The apparatus of claim 17 wherein the memory for storing instructions which, when executive by the one or more processors, causes the one or more processors to update one or more rules for generating therapy profile modification.

29. One or more storage devices having processor readable code embodied thereon, the processor readable code for programming one or more processors to fine tune therapy profile, comprising:
receiving a respective data set from an infusion device and an analyte monitoring device for a predetermined time duration;
time synchronizing the received respective data set;
detecting one or more marked data from the one or more respective data set received;
performing automated data analysis based on the detected one or more marked data to generate a modification to the therapy profile; and
providing the generated modification to the therapy profile.

* * * * *